United States Patent [19]

Domingues

[11] Patent Number: 5,494,686
[45] Date of Patent: Feb. 27, 1996

[54] SUBSTRATE-LIMITED YEAST-LEAVENED REFRIGERATED DOUGH PRODUCTS

[75] Inventor: David J. Domingues, Plymouth, Minn.

[73] Assignee: The Pillsbury Company, Minneapolis, Minn.

[21] Appl. No.: 144,236

[22] Filed: Oct. 27, 1993

Related U.S. Application Data

[63] Continuation-in-part of Ser. No. 732,081, Jul. 18, 1991, abandoned, and Ser. No. 829,453, Jan. 31, 1992, abandoned.

[51] Int. Cl.$^6$ .................................................. A23L 1/05
[52] U.S. Cl. .................... 426/8; 426/19; 426/27; 426/62
[58] Field of Search .................... 426/8, 27, 62, 426/19

[56] References Cited

U.S. PATENT DOCUMENTS

| | | |
|---|---|---|
| Re. 28,074 | 7/1974 | Smerak et al. . |
| 1,232,758 | 7/1917 | Blacklock . |
| 2,043,139 | 6/1936 | Wille et al. . |
| 2,333,764 | 11/1943 | Burgeson . |
| 2,478,618 | 8/1949 | Armstrong et al. ............. 426/128 X |
| 3,096,178 | 7/1963 | Tucker . |
| 3,348,951 | 10/1967 | Evans . |
| 3,995,066 | 11/1976 | Muys et al. . |
| 4,192,918 | 3/1980 | Stineman et al. .................... 435/256 |
| 4,346,115 | 8/1982 | Clement et al. . |
| 4,381,315 | 4/1983 | Yong et al. . |
| 4,406,911 | 9/1983 | Larson et al. . |
| 4,500,548 | 2/1985 | Silva . |
| 4,547,374 | 10/1985 | Nakatomi et al. . |
| 4,693,898 | 9/1987 | Nakatomi et al. . |
| 4,792,456 | 12/1988 | Katz et al. . |

FOREIGN PATENT DOCUMENTS

| | | |
|---|---|---|
| 0145367 | 6/1985 | European Pat. Off. . |
| 0305071 | 3/1989 | European Pat. Off. . |
| 0442575 | 8/1991 | European Pat. Off. . |
| 384114 | 12/1932 | United Kingdom . |
| 1007280 | 10/1965 | United Kingdom . |
| 1587296 | 4/1991 | United Kingdom . |

OTHER PUBLICATIONS

Hino, et al., "New Freeze–Tolerant Yeast for Frozen Dough Preparations", 6031 *Cereal Chemistry* 64(4):269–275.
Singh, et al., "Growth Analysis of Mutations Affecting Growth of *Saccharamyces cerevisiae* at Low Temperature", *Genetics*, 77:651–659 (Aug., 1974).
Ursic, et al., "A Cold–Sensitive Mutant of *Saccharomyces cerevisiae* Defective in Ribosome Processing", *Molec. gen. Genet.* 175, 313–323 (1979).
Finney, "A Review of Older and Some Newer Short–Time Bread Baking Studies," *The Bakers Digest*, vol. 51, No. 5, Oct. 1977, pp. 81–86.
Harrison, et al., "Phosphilpid Breakdown in Baker's Yeast During Drying", Nature [200] pp. 1189–1190 (1963).
Herrera, et al., "Loss of Cell Constituents On Reconstitution of Active Dry Yeast", Arch. Biochem. and Biophys. [63] 131–143 (1956).

*Primary Examiner*—Helen Pratt
*Attorney, Agent, or Firm*—Edward Hotchkiss; Aleya Rahman; Janal M. Kalis

[57] ABSTRACT

A refrigeratable yeast-leavened dough composition and methods of making such dough. The dough composition and the strain of yeast used are chosen to limit the total leavening action of the yeast by controlling the amount of substrate in the dough fermentable by the yeast. The dough compositions are capable of being leavened at elevated temperatures, yet stored in a sealed container at refrigeration temperatures for extended periods of time. A maltose negative yeast is used and sucrose or the like is added to the dough to serve as a fermentable substrate for the dough; this dough is suitable for storage times of up to 30 days or so. At refrigeration temperatures, the yeast used in the dough is substantially incapable of fermenting carbohydrates native to the dough and a predetermined quantity of a non-native carbohydrate fermentable by the yeast (e. g. galactose) is added to the dough to provide the desired amount of proofing.

6 Claims, 13 Drawing Sheets

SUBSTRATE-LIMITED YEAST-LEAVENED REFRIGERATED DOUGH PRODUCTS

This application is a continuation-in-part of application Ser. No. 07/732,081, filed Jul. 18, 199 1, now abandoned, entitled "Yeast-Leavened Refrigerated Dough and Process for Making the Same" and Ser. No. 07/829,453 filed Jan. 31, 1992, now abandoned. The teachings of these co-pending applications are incorporated herein by reference.

FIELD OF THE INVENTION

The present invention relates to refrigeratable dough products for use in making edible baked goods. In particular, the invention provides a yeast-leavened dough which can be stored for extended periods of time at refrigeration temperatures.

BACKGROUND OF THE INVENTION

A wide range of refrigeratable dough products are currently available to consumers for producing numerous different baked products. These refrigerated doughs range from doughs for biscuits and breads to sweet rolls to cornbread products. These dough products are rather popular with consumers because they are very convenient and easy to use. Most of these products are sold in a pre-proofed state so that they can be opened to remove the dough and the dough can be baked immediately. Packaging and selling doughs in a pre-proofed state omits any necessity on the part of the consumers to carefully proof the dough for an extended period of time before baking it.

In producing refrigeratable dough products, suitably sized portions of unproofed dough are placed in individual containers. The dough is then proofed within the container, such as by holding the dough at an elevated temperature, causing the dough to expand. The dough will continue to proof until a positive internal pressure of about 15–20 psi is attained; most such containers will rupture or explode if the internal pressure of the container substantially exceeds about 40 psi. Such products are desirably capable of storage at refrigeration temperatures for at least a couple of weeks, and desirably as long as a few months, without any significant degradation of the quality of the dough or any substantial likelihood of having the containers rupture.

One disadvantage of refrigeratable dough products on the market today is that these doughs generally cannot be leavened with yeast. When yeast is used in a dough, the yeast cells will tend to continue to grow, or at least continue metabolization, even at refrigeration temperatures. The yeast therefore continues to produce carbon dioxide over the entire storage time, unless the dough is stored in a frozen state. Although allowing yeast to ferment for the entire shelf life of the dough may work if the dough is intended to be used immediately, extended storage (e.g. about two weeks or more) in a sealed container generally will not work because the pressure in the container will quickly build and rupture the container. If a conventional yeast-leavened dough were placed in a standard dough product container, the container may be expected to fail in no more than about two days. Additionally, continued activity of the yeast beyond the desired degree of proofing can deleteriously affect the organoleptic and rheological properties of the dough, producing unacceptable final baked products.

To date, manufacturers of refrigeratable doughs have had to replace yeast with chemical leavening agents, such as baking soda or the like. Such chemical leavening agents generally comprise a combination of a leavening acid and a leavening base, with the acid and base portions reacting to generate carbon dioxide, causing the dough to rise. One of the primary advantages of such leavening agents is that their behavior is based upon a predictable chemical reaction, permitting one to readily control the volume of carbon dioxide produced to leaven the dough. Once the chemical reaction of the leavening agents has proceeded to completion, carbon dioxide production ceases.

Although a chemically leavened dough product can be stored for extended periods of time at refrigeration temperatures, the final baked product obtained by baking such a dough is noticeably inferior to a product made with a yeast-leavened dough. Products made from yeast-leavened doughs are widely acknowledged to have superior taste, aroma and texture than those made with chemical leavening agents. Commercial dough manufacturers frequently add ingredients for the sole purpose of simulating yeast-leavened doughs. For instance, these manufacturers frequently add yeast flavoring, such as inactive pasteurized yeast cultures, to the chemically leavened dough. Even with such additives, baked products made from chemically leavened doughs lack the characteristic flavor and aroma of yeast-leavened dough and continue to exhibit relatively poor texture.

Others have attempted to solve the problems associated with storage of yeast-leavened doughs by storing the doughs at freezing temperatures rather than refrigeration temperatures. Frozen yeast-leavened doughs can yield baked goods which are noticeably better than chemically leavened refrigerated doughs. Yeast becomes inactive when frozen, thereby avoiding the problems associated with continued carbon dioxide evolution at refrigeration temperatures.

In a published European patent application (Published European Patent 0 442 575, published 21 Aug. 1991), Gist-Brocades describes a dough composition which uses a substrate limitation concept. In accordance with this disclosure, a dough is leavened with a maltose negative yeast (a yeast which cannot ferment maltose) and the dough is frozen. Gist-Brocades states that the dough may be thawed, proofed and baked anytime the same day without having to carefully monitor the proofing time. However, this dough is not designed by Gist-Brocades to be stored at refrigeration temperatures for extended periods of time, e.g. two weeks or more.

However, frozen doughs simply are not as convenient as pre-proofed refrigerated dough products. Whereas such refrigerated doughs can be baked immediately after removal from the container, frozen doughs must be allowed to thaw prior to baking. Also, since proofed dough does not survive freezing very well, frozen doughs generally must be proofed after thawing and prior to baking. This can further delay the baking of the dough. The consumer must spend more time monitoring the proofing process to avoid over-proofing the dough, making sure to place the dough in the oven for baking at the right time. Not only do such frozen doughs require more attention than do refrigerated dough products, it also requires the consumer to plan well in advance so the dough can be thawed and proofed to provide the baked goods at the desired time.

Hence, there has been a long-felt need in the industry for a yeast-leavened dough that can be stored at refrigeration temperatures for extended periods of time. To date, though, commercial producers have apparently been unable to make and sell refrigeratable yeast-leavened doughs suitable for large-scale commercial production and extended shelf life, despite the obvious economic potential of such a product. It appears that the problems associated with the continued generation of carbon dioxide by the yeast have precluded any such product.

SUMMARY OF THE INVENTION

The present invention provides a diploid yeast useful in making refrigeratable yeast-containing doughs and dough products made therewith. In another aspect, the invention provides a yeast-leavened refrigeratable dough composition. In accordance with one embodiment of the invention, a preselected strain of yeast is mixed with flour and water and, perhaps, other ingredients to form a dough. The yeast and the dough composition are chosen so that the total amount of carbohydrate or carbohydrates fermentable by the yeast in the dough is limited.

The yeast of the invention, referred to below as a "GAL+" yeast, is substantially incapable of fermenting carbohydrates native to wheat flour. In a dough composition of the invention, the yeast is substantially incapable of fermenting carbohydrates native to the flour used in the dough and a non-native carbohydrate, such as galactose, is added to the dough in an amount selected to provide the desired volume of carbon dioxide. By so doing, one may limit the maximum volume of carbon dioxide which the yeast can generate. This, in turn, prevents generation of sufficient carbon dioxide to rupture a sealed container of dough, even if the temperature of the dough is inadvertently elevated.

In accordance with a further embodiment of the invention, the yeast is substantially incapable of fermenting carbohydrates native to wheat flour and is low temperature sensitive. As used herein, "low temperature sensitive" yeast (or simply "lts" yeast) is active at elevated temperatures in the presence of fermentable substrate, but becomes substantially inactive, i.e. substantially ceases producing carbon dioxide, at refrigeration temperatures. Thus, the yeast of this particular embodiment of the invention can be said to be both "GAL+" and "lts".

A method according to the invention comprises making a dough containing flour, water and GAL+/lts or diploid GAL+ yeast and storing the dough at refrigeration temperatures for an extended period of time. Flour, water and lts yeast are mixed together to form the dough. The method may also include the additional steps of placing the resultant dough in a pressurizable container and heating the dough within the container to an elevated temperature for proofing. Once the dough in the container has been proofed, the temperature of the dough within the container is maintained at refrigeration temperatures, preferably for an extended period of time. A method of this embodiment may also further comprise the step of removing the dough from the container and baking it to produce a baked good.

DETAILED DESCRIPTION OF THE PREFERRED EMBODIMENTS

Figure 1:
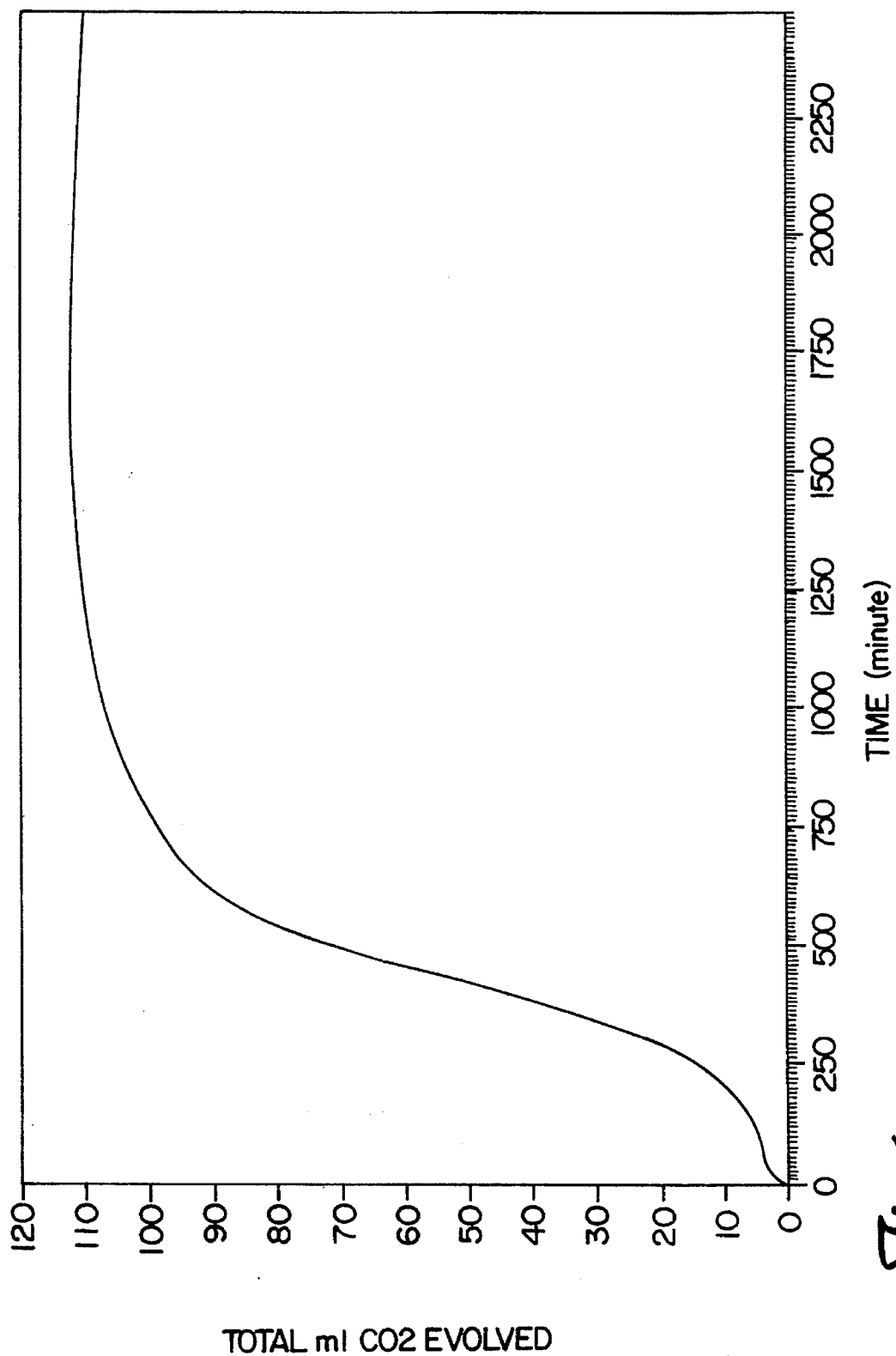
FIG. 1 is a graph showing the volume of carbon dioxide generated by MAL- yeast in a dough composition heat treated at 32° C.

In accordance with the present invention, a dough product is prepared wherein the dough composition and the yeast used therein are chosen in a manner that effectively and controllably limits the leavening action of the yeast by controlling the amount of substrate fermentable by the yeast in the dough. Strains of yeast which do not ferment certain carbohydrates are known in the art; often, two different strains of the same species of yeast are unable to ferment the same sugars. Therefore, a strain of yeast may be utilized in a dough composition which is capable of fermenting only selected sugars. By controlling the total amount of those sugars in the dough composition, the amount of fermentation can be controlled.

As explained above, even at refrigeration temperatures, most yeast will generate carbon dioxide. If the sugar substrate fermentable by the yeast is limited, carbon dioxide generation will substantially cease when the sugar is exhausted. Hence, by either allowing the yeast to metabolize the fermentable sugars in the dough for a given period of time prior to canning or controlling the sugar content of the dough, carbon dioxide generation by the yeast can be substantially terminated once a certain predetermined volume has been reached, regardless of the temperature of the dough. Accordingly, the total volume of carbon dioxide generated in the container can be prevented from reaching a level sufficient to increase internal pressure and rupture the container.

Wheat flours used in most commercial dough manufacturing operations contain about 5 weight percent (wt. %) of damaged starch. Alpha- and beta-amylases (inherent in wheat flour) convert such starch into maltose, among other sugars. Maltose and some of the other sugars produced by the action of the amylase are metabolizable by many strains of yeast.

In an earlier embodiment of the invention, a strain of yeast which did not ferment maltose, referred to as "maltose negative," or just "MAL-," was chosen. Such yeast can usually ferment other types of sugars, such as sucrose or dextrose. A number of yeasts which ferment sucrose but not maltose ("SUC+/MAL-") are commercially available, including the following strains of *Saccharomyces Cerevi-*

*siae:* DZ (CBS 109.90), DS 10638 (CBS 110.90), DS 16887 (CBS 111.90) V 79 (CBS 7045), and V 372 (CBS 7437). Approximately 100–200 ml of CO2 per 100 grams of dough at 32° C. is usually sufficient for proofing. The total amount of fermentable sugar in the dough was adjusted in an attempt to limit the volume of carbon dioxide gas produced by fermentation of the entire fermentable sugar supply.

EXAMPLE 1

In order to test a dough product leavened with a MAL-yeast as a means of providing a refrigeratable yeast-leavened dough composition, water and a MAL- yeast were slurried together to produce a total combined weight of approximately 194 grams. The slurry contained 189 grams of water and 4.8 grams of the yeast. The yeast used in making the slurry was a MAL- strain of yeast which was obtained in a paste form. The paste was mixed with water at room temperature (approximately 23° C.) and allowed to sit at room temperature for about 10–15 minutes.

To this slurry was added 261.74 grams of flour, 18.77 grams of wheat gluten pre-blend, 3.60 grams of salt and 1.20 grams of dextrose. The wheat gluten pre-blend was 75 wt. % vital wheat gluten, 21.9 wt. % hard, high gluten, enriched ingredient flour, 2.50 wt. % xanthan gum, and 0.616 wt. % azodicarbonamide premix. The resulting dough composition therefore contained 54.53 wt. % flour, 3.91 wt. % gluten pre-blend, 0.75 wt. % salt, and 0.25 wt. % dextrose, with a final concentration of 1.00 wt. % MAL yeast.

The dough composition was mixed in a Farinograph™ mixing bowl at 60 rpm for 4.5 minutes. Immediately after mixing, a 50-gram sample of the dough composition was placed into a Risograph™ testing machine. The Risograph is commercially available from Sheldon Manufacturing, Inc. for detecting the volume of gas, e.g. carbon dioxide, generated by a sample and the rate at which the gas is generated.

Figure 2:
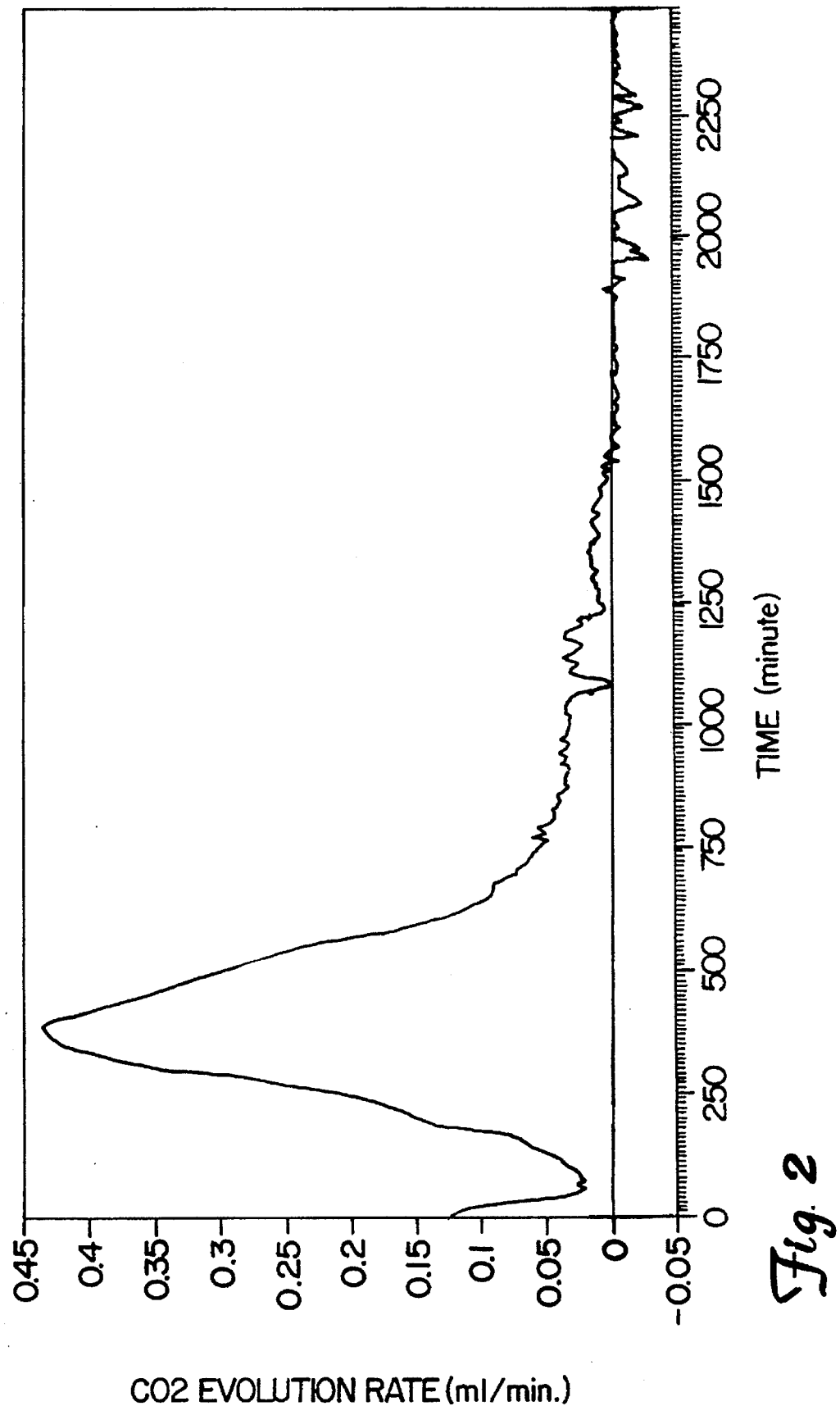
FIG. 2 shows the rate of carbon dioxide evolution for the dough shown in FIG. 1.

FIGS. 1 and 2 show the data collected in the Risograph for the sample. Of particular interest, the dough appeared to effectively cease producing carbon dioxide after about 1500 minutes at 32° C. Dough products made with this dough by placing the dough in standard spirally wound refrigeratable dough containers were found to maintain acceptable internal pressures, e.g., below about 20 psi, for about 25 days. However, carbon dioxide once again began to be generated by the dough after about 25 days. This renewed activity of the yeast in the dough was projected to be sufficient to generate enough carbon dioxide to cause all of the containers of Example 1 to rupture after about 50–55 days.

It has not been conclusively determined why the yeast became active after apparently substantially ceasing fermentation. However, one factor which is believed to have contributed to the generation of additional carbon dioxide, and subsequent failure of the containers, is a change in the carbohydrates present in the dough. As noted above, alpha- and beta-amylases, which are inherent in wheat flours, act on carbohydrates present in the dough, and particularly in the flour. Over time, these amylases break down oligosaccharides which are not fermentable by the yeast, such as maltose and maltotriose, into sugars which can be fermented by the yeast. Accordingly, it is anticipated that, even if the yeast used in such a dough composition were truly maltose negative, the changing carbohydrate profile of the dough may present sugars which are fermentable by the yeast. Accordingly, the dough could continue to generate carbon dioxide and cause containers to rupture.

Thus, a dough product made with a MAL- yeast and a limited amount of initial maltose in the composition can be useful for storage at refrigeration temperatures for shorter periods of time, with a storage period on the order of about 30 days or less. If such dough products were stored for significantly longer periods of time, it is likely that the containers would begin to fail. Although a shelf life of 30 days may be suitable for some applications, current refrigerated dough products are expected to have an anticipated shelf life at refrigeration temperatures of 90 days or more. Accordingly, this MAL- embodiment of the invention may have only limited commercial application, with commercial use being limited to institutional markets, such as in-store bakeries and the like, where an anticipated shelf life of 30 days may nonetheless be considered acceptable.

In accordance with a preferred embodiment of the present invention suitable for significantly longer storage at refrigeration temperatures, the strain (or strains) of yeast used in the dough are substantially incapable of fermenting carbohydrates which are native to the flour. In the case of doughs using wheat flour, these native carbohydrates include sugars such as maltose, sucrose, glucose, fructose and various oligosaccharides made up of these sugars. If other flours were to be used, of course, there may be some variation in the sugars native to such a flour.

Use of such a yeast has been found to effectively prevent the yeast from fermenting any carbohydrates in the dough which are either initially present in the dough composition or result from the action of alpha- and beta-amylases on the carbohydrates initially present in the dough. A predetermined quantity of a non-native carbohydrate which is fermentable by the yeast may be added to the dough to provide the desired amount of proofing. Once that substrate is consumed, the fermentation activity of the yeast appears to substantially cease, preventing further carbon dioxide generation and avoiding overfermentation of the dough. It has been found that dough compositions in accordance with this embodiment of the invention can be used to make dough products which can be stored for periods of time in excess of 90 days without rupturing or exploding.

The non-native carbohydrate which can be fermented by the yeast strain in the present dough can be virtually any carbohydrate which does not naturally occur in the flour. This carbohydrate is preferably a sugar or an oligosaccharide, though. For instance, the fermentable, non-native sugar may be galactose or lactose, a disaccharide of glucose and galactose.

In one particularly preferred embodiment, the yeast is capable of fermenting galactose, which is not native to wheat flours, but is substantially unable to ferment any sugars which are native to wheat flour; this yeast is referred to below as a "galactose positive" or "GAL+" yeast. This GAL+ yeast is mixed with flour, water and galactose to form a dough. The amount of galactose in the dough is selected to limit the activity of the yeast so that the dough is proofed no more than the desired degree. As noted above, in most circumstances about 100–200 ml of carbon dioxide per 100 grams of dough at 32° C. is sufficient to proof the dough. Accordingly, the weight percentage of galactose in the dough composition should be chosen to generate no more than approximately 200 ml of carbon dioxide per 100 grams of dough at 32° C. The amount of galactose necessary to generate this volume of carbon dioxide will have to be determined on a case-by-case basis as the amount may vary for different strains of yeast.

Given the present disclosure, it will be well within the ability of those skilled in the art to make yeasts which are substantially incapable of fermenting carbohydrates native to flour but capable of fermenting other carbohydrates. Such yeasts can be made through standard methods of crossing yeast strains, isolating suitable strains having the desired properties and the like. These types of common techniques are described, for example, by Sherman et al. in *Methods in Yeast Genetics*, the teachings of which are incorporated herein by reference. Of particular interest in Sherman et al. is Section III, entitled "Making Mutants", which appears on pages 273–369 of this reference.

Lobo and Maitra teach a method of rendering a hexokinase negative yeast strain (e.g. a yeast strain incapable of producing hexokinase and of the genotype hxk1, hxk2) glucokinase negative (i.e., a method for making a GAL+ yeast strain) using standard techniques in "Physiological Role of Glucose-Phosphorylating Enzymes in *Saccharomyces cerevisiae*," *Archives of Biochemistry and Biophysics* 182, 639–645 (1977), the teachings of which are incorporated herein by reference. In accordance with that method, the hexokinase negative strain was mutagenized with N-methyl-N'-nitro-N-nitrosoguanidine in yeast extract-peptone medium (YEP) containing 50 mM glucose-free galactose, and a glucokinase-negative mutant was isolated by replica plating from a YEP galactose plate to a YEP glucose plate as a glucose-negative colony. The genotype of the mutuant, determined by independent genetic analysis, was hxk1 hxk2 glk1, where hxk1 and hxk2 stand for genes coding P1 and P2 hexokinases respectively, and glk1 for the genetic determinant for glucokinase synthesis.

Although Lobo and Maitra teach one suitable method of making a yeast for use in accordance with the present invention, others methods will be apparent to those of skilled in the art. Those in the art will also realize that other strains of yeast which are substantially incapable of fermenting carbohydrates native to a particular flour but capable of fermenting non-native carbohydrates other than galactose can be made by known methods.

EXAMPLE 2

In order to test the ability of a GAL+ yeast to ferment carbohydrates which are native to a common dough system, a dough composition containing GAL+ yeast was prepared. This dough formula included 870.75 g (58.05 wt. %) wheat flour, 529.80 g (35.32 wt. %) water, 58.20 g (3.88 wt. %) of the wheat gluten preblend used in Example 1, 11.25 g (0.75 wt. %) salt and 28.50 (2.00 wt. %) yeast. The yeast used in this experiment was a GAL+ strain of *Saccharomyces Cerevisiae* designated as D308.3; this yeast was of the genotype α hxk1 hxk2 glk1 ade1 trp1 his2 met4. This yeast is available to the public from the Yeast Genetic Stock Center at the Donner Laboratory in the Department of Molecular and Cell Biology of the University of California, Berkley (YGSC); in the Seventh Edition of the catalog of the YGSC dated Mar. 15, 1991, this strain of yeast was listed under stock no. D308.3. This yeast strain was also deposited with the American Type Culture Collection of 12301 Parklawn Drive, Rockville, Md. 20852, USA (ATCC), on 5 Mar. 1993, under number ATCC 74211.

Isolated colonies of the D308.3 yeast from solid galactose agar plates were used to inoculate six 50 ml culture flasks containing liquid yeast extract-peptone ("YEP") and galactose. The samples were incubated for approximately 20 hours at about 30° C. and then used to inoculate six one-liter flask samples, which also contained YEP and galactose. These 1 L flasks were incubated for about 24 hours at 30° C., followed by incubation at about 24° C. for approximately 20 hours.

This yeast was then harvested using a GSA rotor, which is commercially available from Sorval Instruments. Sample containers for use with the GSA rotor were filled so that the total weight of the sample, lid and container was about 300 g. The sample container was spun at 2500 rpm for 20 minutes, and the supernatant fluid was immediately decanted. Enough distilled water to raise the total weight of the sample, lid and container to 300 g was added to the sample container, and the container was swirled to bring the yeast pellet back into suspension. This sample container was then spun at 2500 rpm for 20 minutes again, and the supernatant fluid was again decanted.

The washed yeast paste and water were combined to form a slurry. This slurry was mixed with the other ingredients in a table-top Hobart mixer. The dough was mixed at speed 1 for 30 seconds, followed by mixing at speed 2 for between about 4 and about 5 minutes. The two 100 g samples (A1 and A2 in FIGS. 3 and 4) and two 50 g samples (A3 and A4 in FIGS. 3 and 4) were placed in the Risograph testing machine used in connection with Example 1 above. The samples were incubated at about 30° C. for about 17 hours (1,000 minutes). The results of this Risograph testing are shown in FIGS. 3 and 4.

Figure 3:
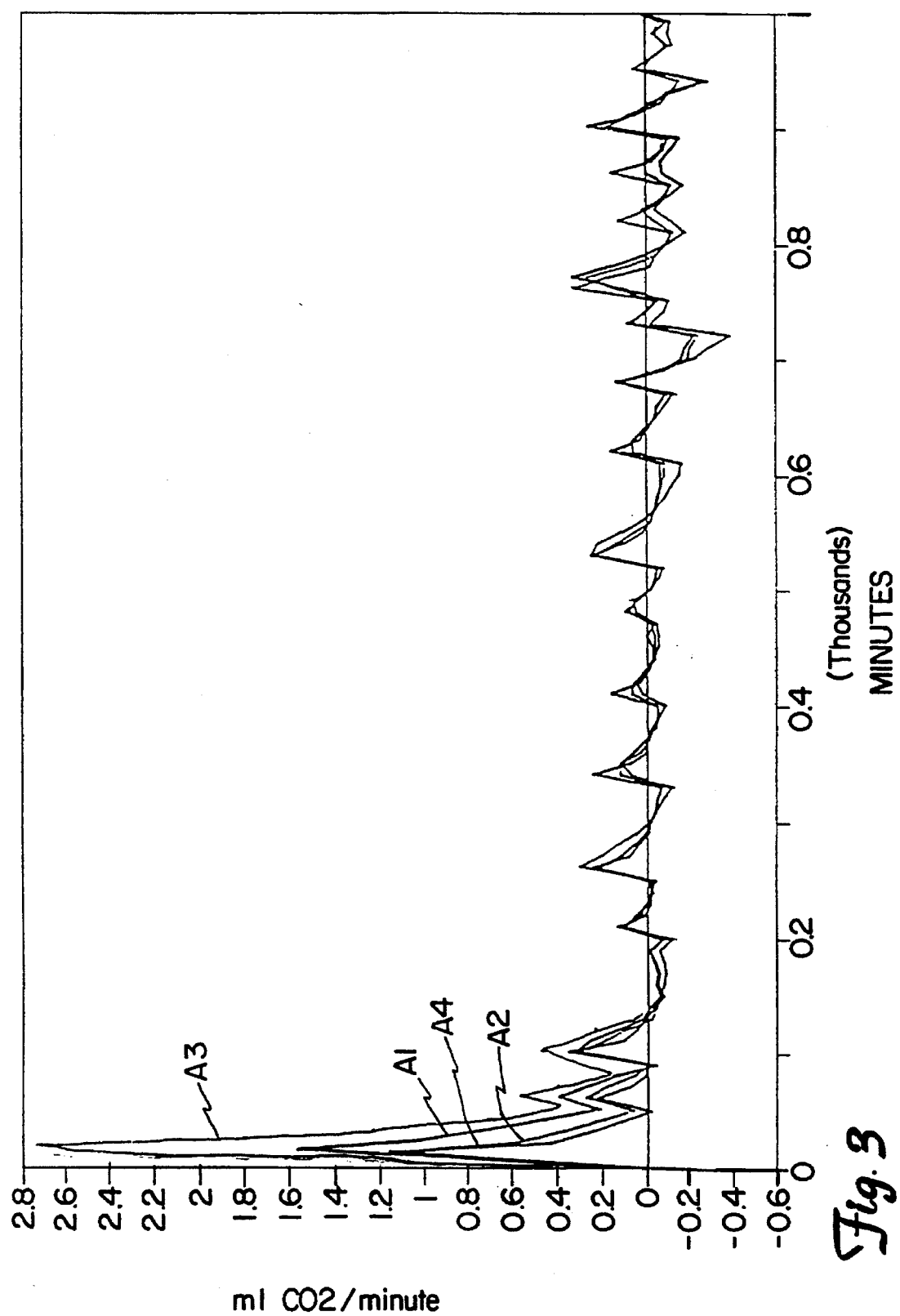
FIG. 3 is a graph depicting the rate of carbon dioxide generation over time for a GAL+ yeast in a dough composition held at 30° C.

As can be seen in FIG. 3, carbon dioxide was generated fairly rapidly in all of these samples for the first 40–50 minutes, after which the rate of evolution tapered off to about zero. Although the rate of carbon dioxide generation appears to have fluctuated between slight positive and negative rates, it appears as though the samples generated very little or no carbon dioxide between about 120 minutes after incubation began and the end of the experiment.

Figure 4:
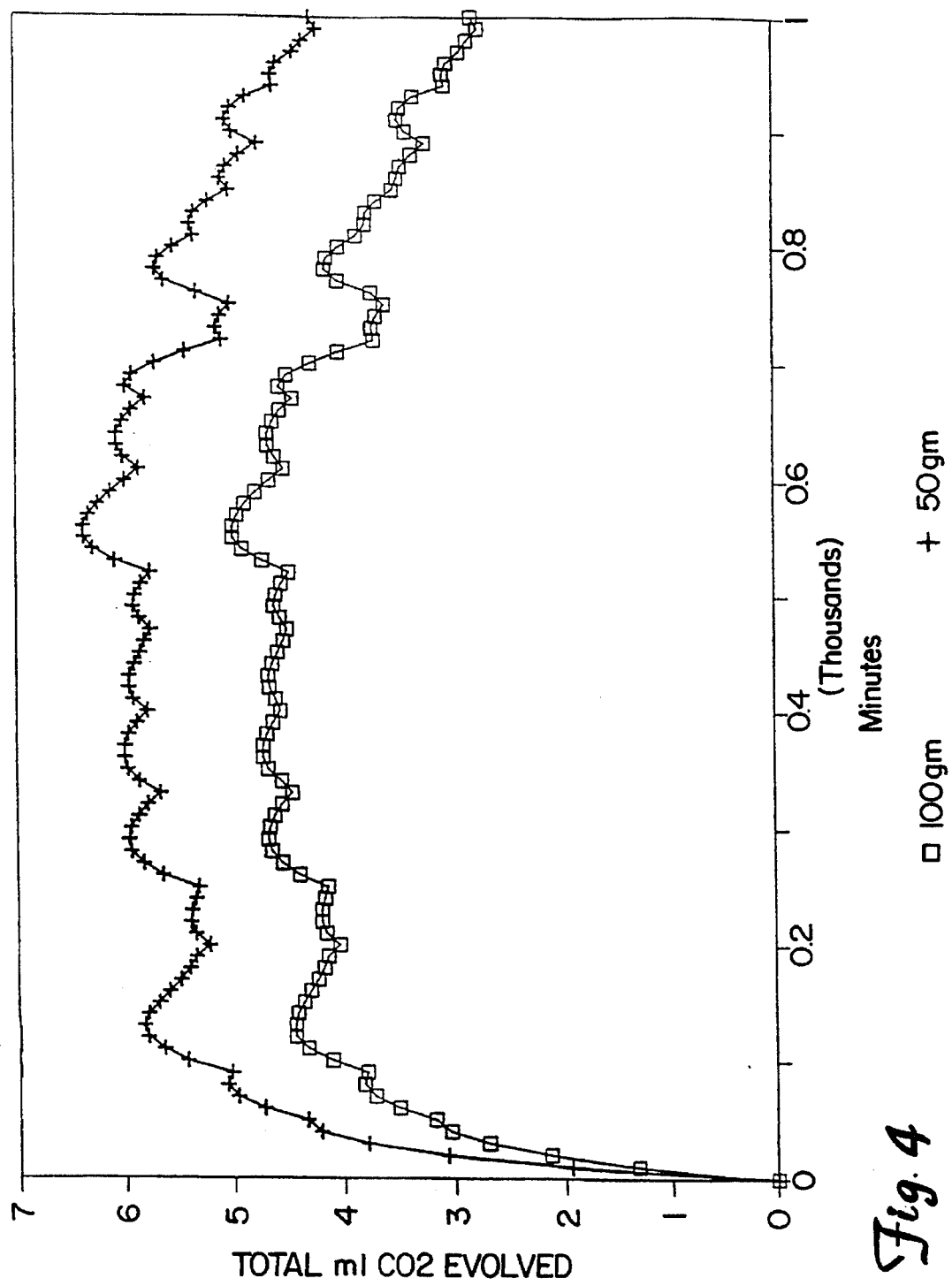
FIG. 4 shows the total volume of carbon dioxide generated in the sample of FIG. 3.

Furthermore, although the rate of carbon dioxide generation was noticeable at the beginning of the experiment, it should be noted that the total volume of carbon dioxide generated in this sample was no more than about 7 ml; this result is best seen in FIG. 4. As noted above, in order to adequately proof dough, between about 100 and about 200 ml of carbon dioxide/100 g of dough is generally considered to be necessary. The volume of carbon dioxide generated in these galactose-free samples, though, fell well below those limits. The indication that about 7 ml of gas was generated in these samples may actually be attributable primarily, if not entirely, to an expansion of the headspace in the Risograph sample containers when the containers were heated for incubation. In other words, it appears likely that no appreciable carbon dioxide was generated by the dough samples in this experiment.

Accordingly, the D308.3 yeast used in this Example can be said to be substantially incapable of fermenting, or otherwise metabolizing, the carbohydrates native to this dough system. Hence, it is believed that the D308.3 strain of yeast can be accurately referred to as GAL+, as that term is used herein, and this yeast provides one example of a yeast suitable for use in the present invention. As noted above, though, one of ordinary skill in the art could make other GAL+ yeasts, as well as other yeasts which are capable of fermenting only carbohydrates not native to the flour in the dough, in light of the present disclosure.

EXAMPLE 3

In order to test the responsiveness of the GAL+ yeast used in Example 2, four different dough compositions, with varying non-native carbohydrates, were prepared. Each of the four doughs included 290.25 g of flour, 176.60 g of water, 3.50 g of salt and 12.00 g of the D308.3 GAL+ yeast used in Example 1. The formulas of the four different doughs varied in the nature of the other ingredients which were added. In a control sample, no other ingredients were added; in a second sample, 5.00 g of galactose was included; in a third sample, 10.00 g of lactose was provided; and the final sample included 20.00 g of non-fat dry milk (NFDM), which is used a flavoring ingredient in some doughs and typically contains some lactose and may contain slight amounts of galactose.

Figure 5:
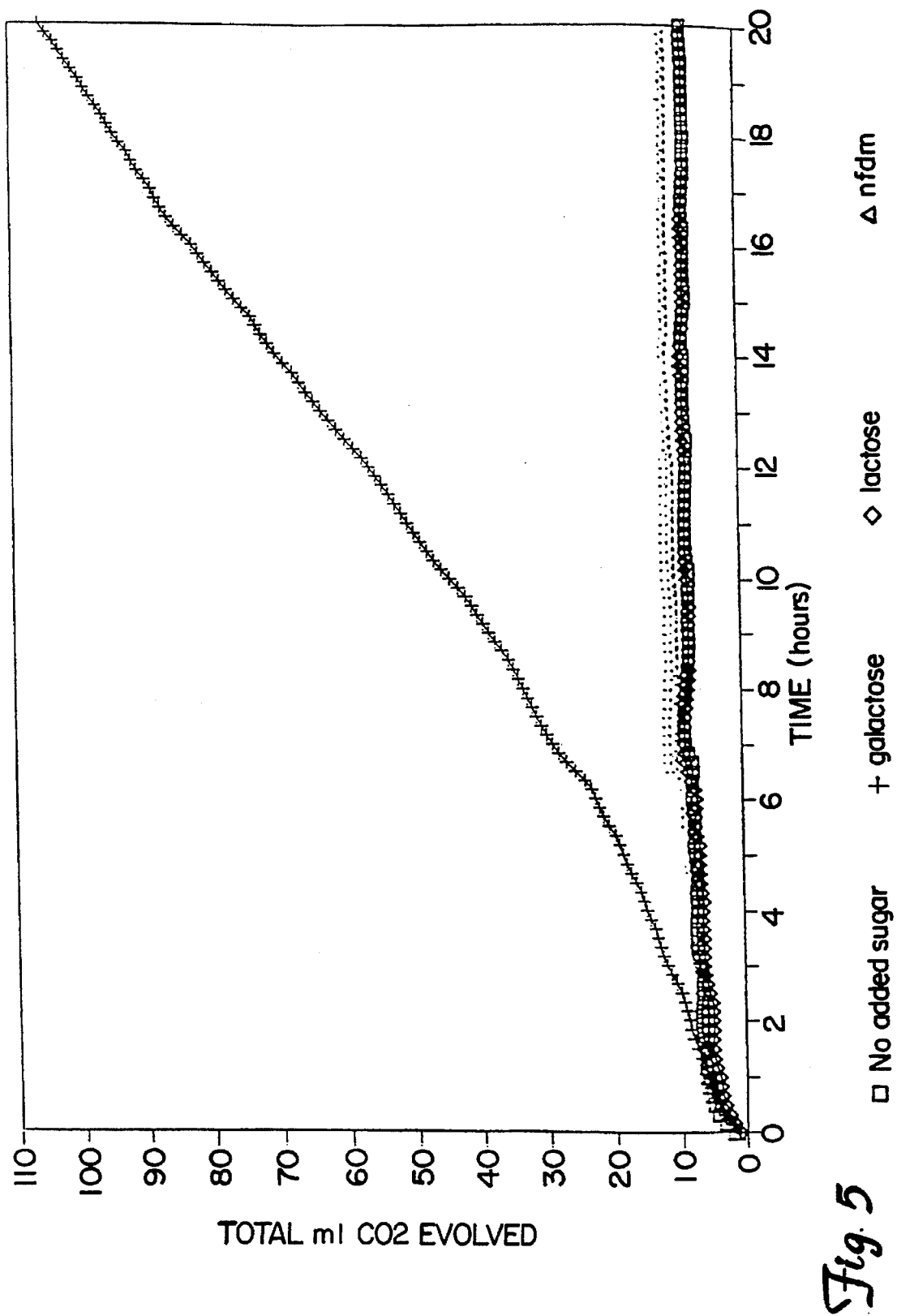
FIG. 5 is a graph showing the total volume of carbon dioxide generated by four dough compositions differing in the nature of non-native carbohydrates added to the dough.
Figure 6:
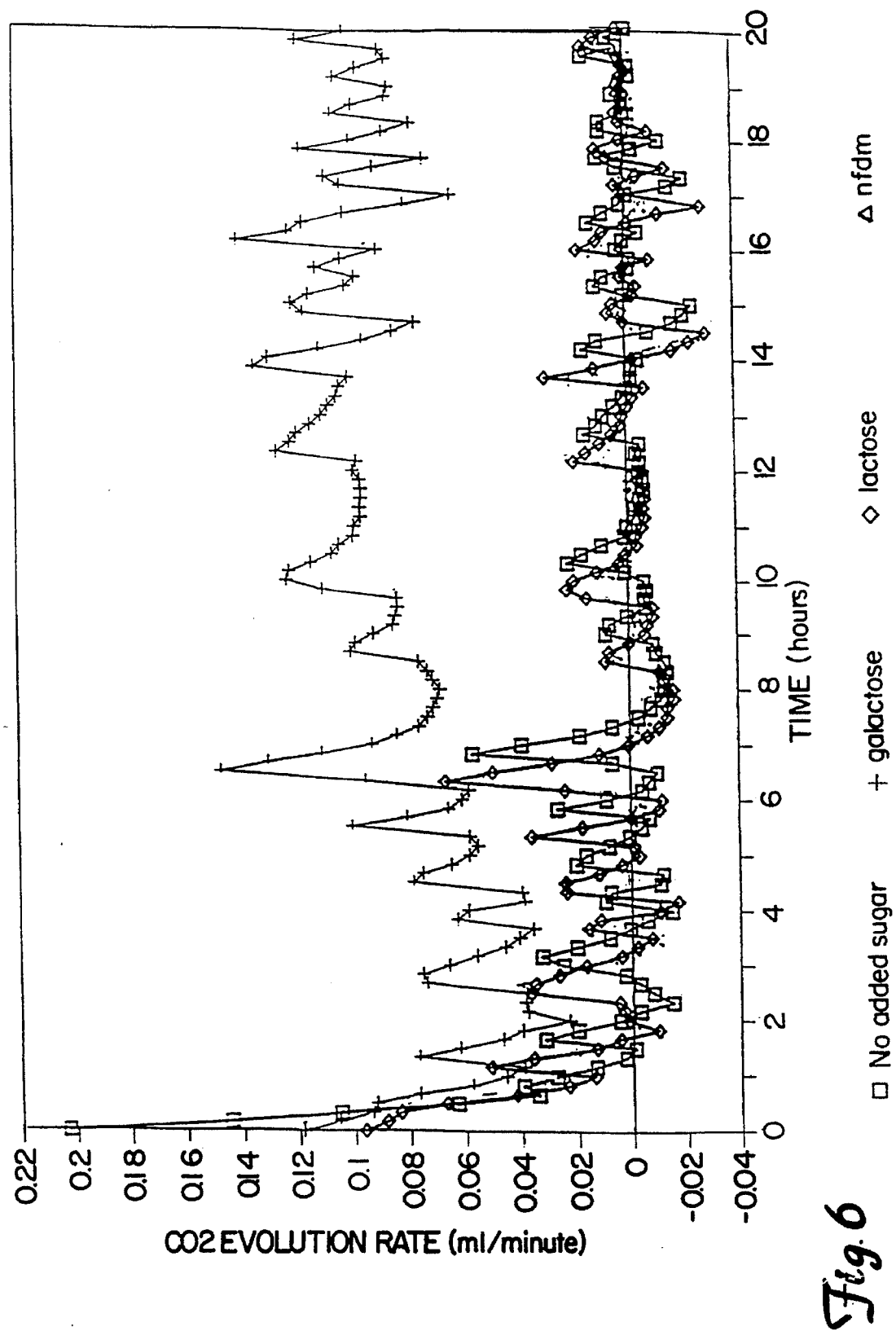
FIG. 6 depicts the rate of carbon dioxide evolution for the doughs shown in FIG. 5.

Yeast paste was grown and harvested in substantially the same manner as set forth in connection with Example 2. For each of the samples, the washed yeast was slurried with the water, and this slurry was added to the other ingredients in a table-top Hobart mixer. Each sample was then mixed at speed 1 for about 30 seconds, followed by mixing at speed 2 for about 4 minutes. Two 100 g samples of each of the dough compositions were placed into Risograph sample jars immediately after mixing and held in the Risograph at about 28° C. for approximately 20 hours. FIGS. 5 and 6 show the total volume of carbon dioxide evolved and the rate of carbon dioxide evolution., respectively, for each of the samples.

As can be seen from FIGS. 5 and 6, only the dough composition which included galactose generated appreciable volumes of carbon dioxide. The control sample, the lactose-containing sample and the sample with the NFDM all generated less than about 10 ml of carbon dioxide over a period of about 20 hours. Furthermore, essentially all of the carbon dioxide generation measured for the non-galactose doughs was generated in the first one to two hours of incubation. This slight change in gas volume in the Risograph sample jars may be wholly attributable due to thermal expansion of the headspace in the sample jars, as explained above. Accordingly, the samples which did not contain non-native galactose quite likely did not generate any significant amount of carbon dioxide during the course of this test.

The results of this experiment show that the D308.3 yeast can metabolize galactose but it is substantially incapable of fermenting any carbohydrates which are native to flour of the dough composition. It also appears that this yeast is substantially incapable of fermenting either "straight" lactose or lactose in non-fat dry milk. During the course of this experiment, the galactose-containing dough appears to continue to generate carbon dioxide, indicating that not all of the galactose was used. Furthermore, at the end of the 20-hour incubation, the galactose dough had generated slightly more than 100 ml of carbon dioxide, with carbon dioxide generation appearing to continue beyond the end of the experiment.

The dough containing galactose was about 1.0 wt. % galactose (5.00 g galactose/487.35 g total dough). Based on the results of this experiment, it appears that about 1 wt. % galactose is more than adequate to generate the desired 100–200 ml of carbon dioxide per 100 g of dough. Additional experimentation using standard, spirally wound composite containers of about 250 cc capacity, such as are commonly used in packaging commercial refrigerated doughs, has established that about 0.5 wt. % to about 1.0 wt. % galactose is sufficient to generate enough carbon dioxide to reach an internal pressure of about 10–20 psi. Accordingly, in making a refrigeratable dough product of the invention, the dough placed in the container optimally includes between about 0.5 wt. % and about 1.0 wt. % galactose.

EXAMPLE 4

The D308.3 yeast was added to a chemically-leavened dough product in order to see if the presence of the GAL+ yeast affected the integrity of the container if no galactose was added to the dough. Two batches of a dough containing the D308.3 yeast and two separate batches of chemically leavened dough were prepared. The chemically leavened doughs had the following formula: about 1590 g (56 wt. %) flour, 947 g (33.43 wt. %) water, 110 g (3.9 wt. %) of the wheat gluten pre-blend of Example 1, 89.2 g (3.15 wt. %) of yeast flavorings, 42.5 g (1.5 wt. %) glucono delta lactone (GDL), 32.0 g (1.13 wt. %) baking soda, and 21.3 g (0.75 wt. %) salt. The two batches of dough containing yeast had a very similar formula, with the approximately 947 g (33.4 wt. %) of water being replaced with about 890 g (31.4 wt. %) of water and about 56.7 g (2.00 wt. %) D308.3 yeast.

The water in each of these batches was first mixed with the flavoring ingredients before being charged with the flour and gluten pre-blend into a McDuffy mixing bowl. In the batches containing yeast, the yeast was slurried with the water before the flavoring ingredients were added to this slurry. The ingredients were mixed at speed 1 for about 30 seconds, followed by mixing at speed 2 for about 5 minutes. The salt and the leavening agents (GDL and soda) were then added to this dough and the mixture was mixed at speed 1 for approximately 30 seconds and at speed 2 for about 2.5 minutes.

Each batch of dough was sheeted to a thickness of about ¼ inch (about 0.64 cm) and rolled into a long "log" of dough. Each log of dough was divided into a series of samples weighing about 210 g and each sample was sealed into a standard, spirally wound composite can having a 250 cc capacity. These dough products were then proofed at about 32–35° C. until an internal pressure of about 10–15 psi in the containers was reached. After this proofing, the dough products were transferred to refrigerated storage at about 4° C.

Figure 7:
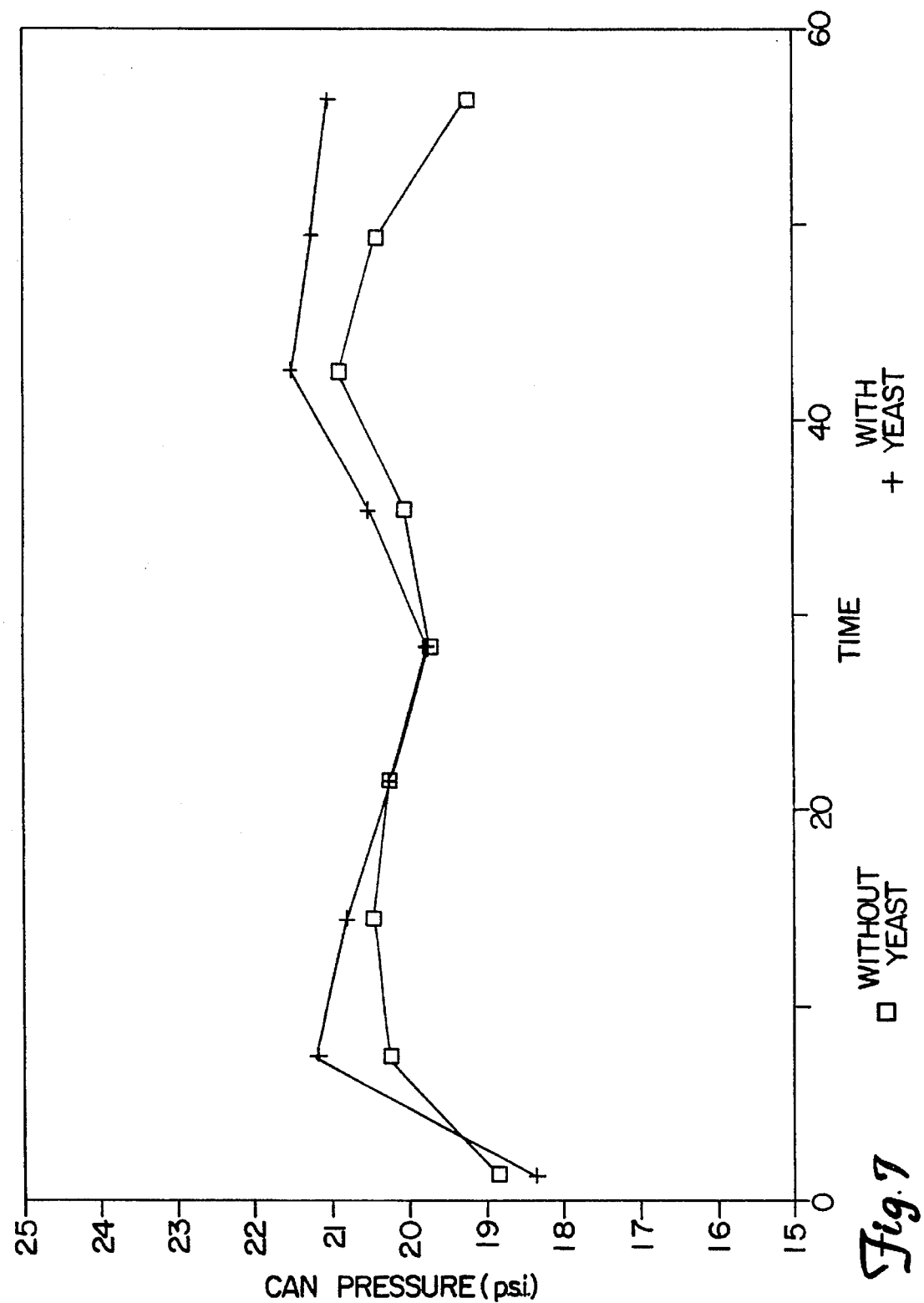
FIG. 7 plots measured can pressure over time for two chemically leavened doughs, one containing a GAL+ yeast, the other without.

FIG. 7 plots the measured can pressure, i.e., the internal pressure of the container, as a function of time. As can be seen in FIG. 7, there does not appear to be any significant difference between the pressure in the dough product containing the standard chemically leavened dough and the dough product containing the chemically leavened dough with the GAL+ yeast.

A variety of other physical measurements were made on the different samples to compare the standard chemically leavened dough with the yeast-doped dough. Among the physical measurements compared were water retention, pH, and sugar content. Samples of the doughs were also baked at approximately 375° F. (163° C.) for about 20 minutes. The specific volume, as well as the appearance, aroma and other sensory properties, of the resulting baked goods were compared. Aside from a slightly lower specific volume for the sample containing the GAL+ yeast, there did not appear to be any significant differences between these two dough compositions.

EXAMPLE 5

The relationship between galactose content of the dough and the resultant internal pressures of dough products containing dough in accordance with the invention was tested. Four different batches were prepared, with the batches differing only in the amount of galactose added. Each dough composition contained about 870.75 g (58.05 wt. %) wheat flour, 529.80 g (35.32 wt. %), water, 58.20 g (3.88 wt. %) of the wheat gluten preblend used in Example 1, 11.25 g (0.75 wt. %) salt and 28.50 g (2.00 wt. %) D308.3 yeast. Additionally, one batch contained about 5.92 g (0.5 wt. %) galactose, another contained about 7.40 g (0.63 wt. % ) galactose, a third contained about 8.87 g (0.75 wt. %) galactose, and the final batch contained about 11.83 g (1.00 wt. % ) galactose.

The D308.3 yeast was grown and harvested in substantially the same manner as that detailed above in Example 2. In forming batches of dough containing the 0.5 wt. % and 1.0 wt. % galactose, the yeast paste was then mixed with the water and the galactose in a 1 L culture flask and incubated in the flask for about 1 hour at about 30° C. while the flask was agitated. This slurry was then added to a McDuffy mixing bowl and mixed with the other ingredients at speed 1 for about 30 seconds, followed by mixing at speed 2 for about 7 minutes. The 0.63 wt. % and 0.75 wt. % galactose batches were prepared slightly differently in that the yeast, water and galactose were not incubated prior to being mixed with the other ingredients. Instead, these three ingredients were slurried in a table-top Hobart and were mixed at speed 2 for only about 4 minutes with a dough hook.

After the doughs were mixed, two 50-gram samples from each batch of dough were placed in Risograph sample jars and incubated in the Risograph at about 28°–30° C. The dough was then rolled, divided into 210-gram samples, and packaged in a standard refrigeratable dough container, as outlined above in Example 4. The resultant dough product was incubated at about 35° C. for about three hours and subsequently stored at about 4° C.

Figure 8:
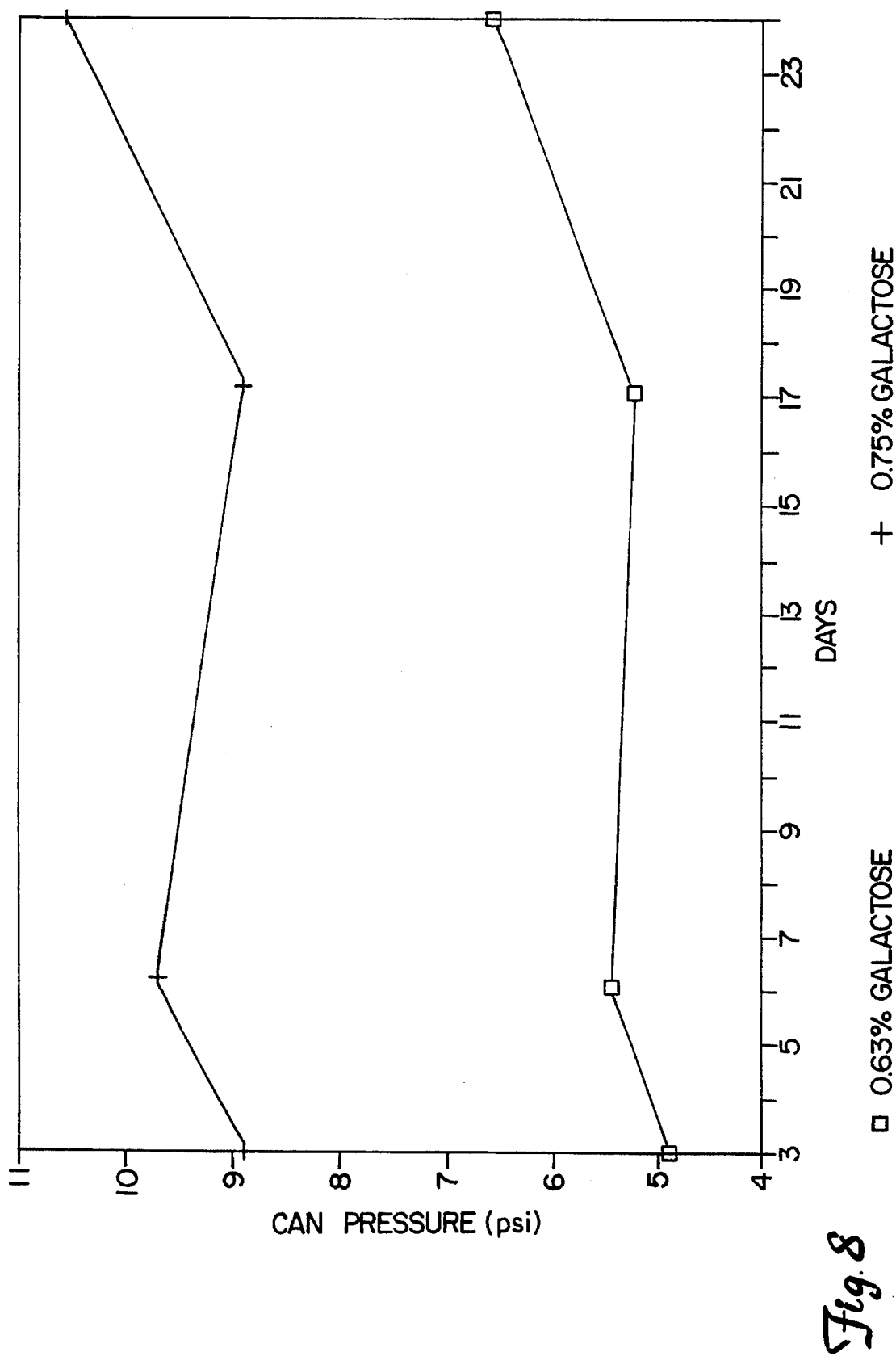
FIGS. 8 and 9 show can pressure over time for three dough samples having different amounts of non-native sugar incorporated in their composition.
Figure 9:
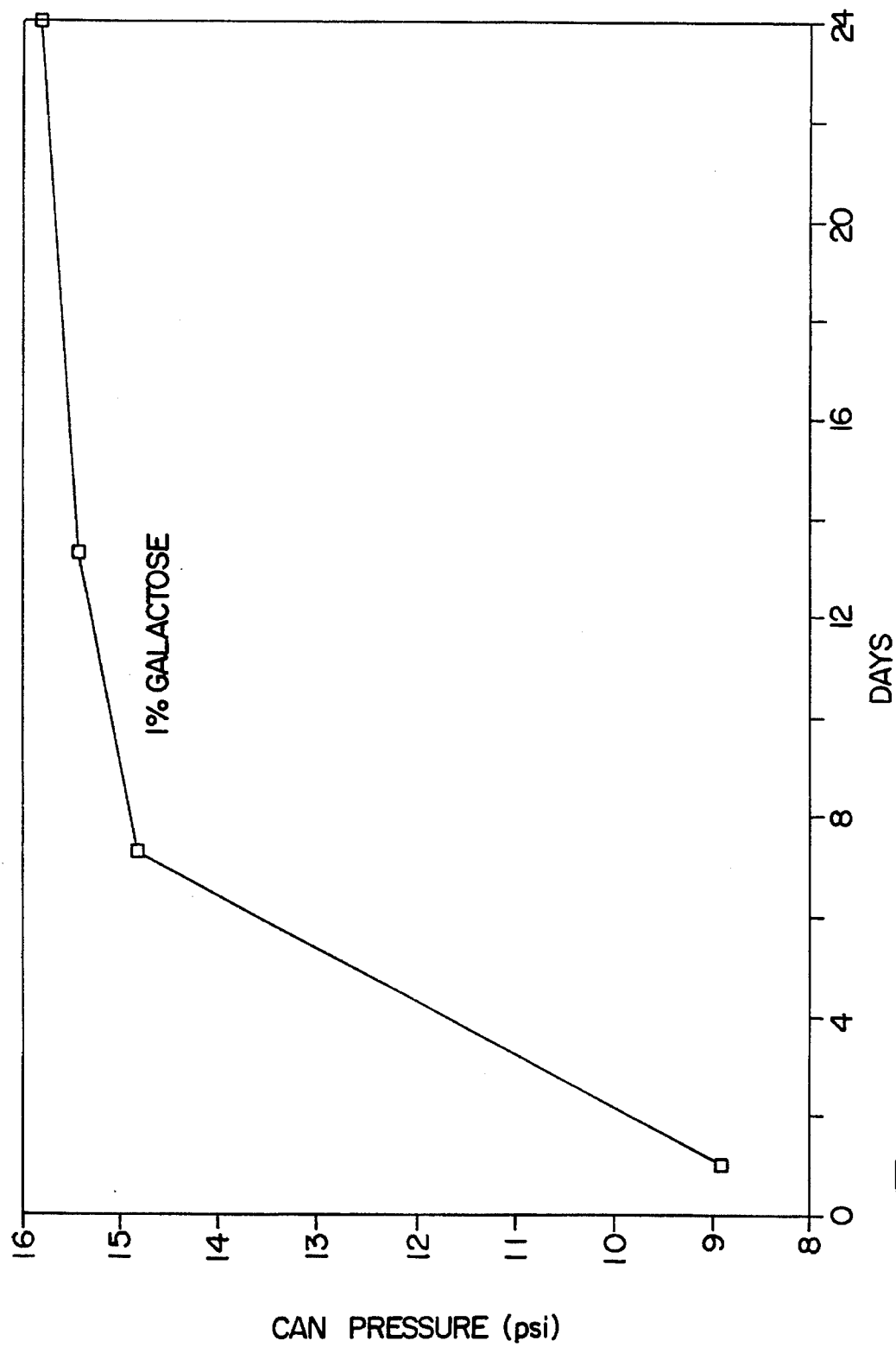

FIGS. 8 and 9 illustrate the can pressures of the samples in the Risograph as a function of time, with the can pressures for samples from each batch being averaged together to generate these plots. It can be seen that the ultimate can pressure of the sample is generally proportional to the amount of galactose in the dough. Whereas the sample containing 0.63 wt. % galactose had a can pressure of about 5–6.5 psi, the 0.75 wt. % dough had can pressures of about 9–10.5 psi and the pressure in the dough with 3 wt. % yeast and 1 wt. % galactose generated a maximum pressure of just under 16 psi. Accordingly, it appears as though the desired pressure in a container of the invention can be fairly readily controlled as a simple function of the amount of galactose added to the dough—once the galactose is exhausted, the dough will substantially cease producing carbon dioxide.

EXAMPLE 6

The D308.3 yeast perhaps adversely affected the sensory appeal of baked doughs containing such yeast in that the final baked product exhibited a slightly off-white color. Although all of the other organoleptic qualities of the dough were exemplary, doughs which would not exhibit this slight discoloration would probably be more appealing to consumers. It was determined that the discoloration of the dough was most likely due to inability of the D308.3 yeast to make adenine, causing the yeast to develop a pinkish or reddish hue when it is grown in a medium without adenine supplementation. This discoloration of the yeast is presumed attributable to a build up of metabolites which are toxic to the yeast (but not to humans).

Spontaneous revertant strains of the D308.3 yeast which do not require adenine for metabolization, referred to herein as RD308.3 yeast, were isolated. First, a concentrated paste of the D308.3 yeast was formed by spinning down the yeast in a rotor, as outlined in Example 2. This yeast paste was then diluted with a potassium phosphate monobasic buffer (about 43 mg $KH_2PO_4$ added to a liter of distilled water, with the pH adjusted to about 7.2 with NaOH) and spread on an "adenine drop out" (ADO) medium, i.e. a medium which does not contain any supplemental adenine, at a concentration of about $1 \times 10^7$ colony forming units (CFU)/ml. The ADO medium contained, for each liter of distilled water, about: 6.7 g of bacto-yeast nitrogen base without amino acids, 20 g galactose, and 20 g of bacto-agar, 2 g of a "drop out mix" which contained alanine, argenine, asparagine, aspartic acid, cysteine, glutamine, glutamic acid, glycine, histidine, inositol, isoleucine, leucine, lysine, methionine, para-aminobenzoic acid, phenylalanine, proline, serine, threonine, tryptophan, tyrosine, uracil, and valine. (Substantially the same formula is taught by Rose et al. in Appendix A of *Methods in Yeast Genetics, A Laboratory Course Manual* (1990), which is incorporated herein by reference, at pages 179–180, but that formula used glucose rather than galactose.)

These ADO plates were incubated at about 25° C. for approximately 4 days and colonies of the yeast which did not require adenine were isolated. Identifying these colonies was greatly simplified by the fact that the non-revertant strains tended to be pinkish or reddish in hue while the revertant colonies were whitish. The isolated yeast was then once again plated onto a fresh ADO medium and incubated under substantially the same conditions. Colonies of revertant strains of the yeast were once again isolated from any strains inadvertently carried over in the first isolation and the platting and incubation were repeated one final time. Although it is believed that one skilled in the art could readily make such a yeast in light of the present disclosure, this resulting strain of RD308.3 yeast has been deposited with the ATCC on 5 Mar. 1993 under number ATCC 74212 and this strain is available to the public from the ATCC.

Two samples were prepared, with one sample containing the original D308.3 yeast and the other containing the RD308.3 yeast. These samples were prepared by mixing an isolated colony (about one loop) of the desired yeast with about 5 ml of YEP/galactose (which contained about 10 g of bacto-yeast extract, 20 g of bacto-peptone, and about 20 g of galactose per 1 liter of distilled water) and incubating for about 12–15 hours at about 30° C. (The formula for the YEP/galactose medium is substantially the same as the YEP/glucose formula taught on page 177 of Appendix A of *Methods in Yeast Genetics*, noted above, except that the glucose in that formula was replaced with galactose in the present medium.) Titer results indicated a population of approximately $48 \pm 2 \times 10^5$ CFU/ml for each strain. For each of the resulting samples, about 100 μl of the sample was added to three separate 5 ml potions of media, with one medium comprising just YEP, another comprising YEP and glucose and the third comprising YEP and galactose.

Figure 10:
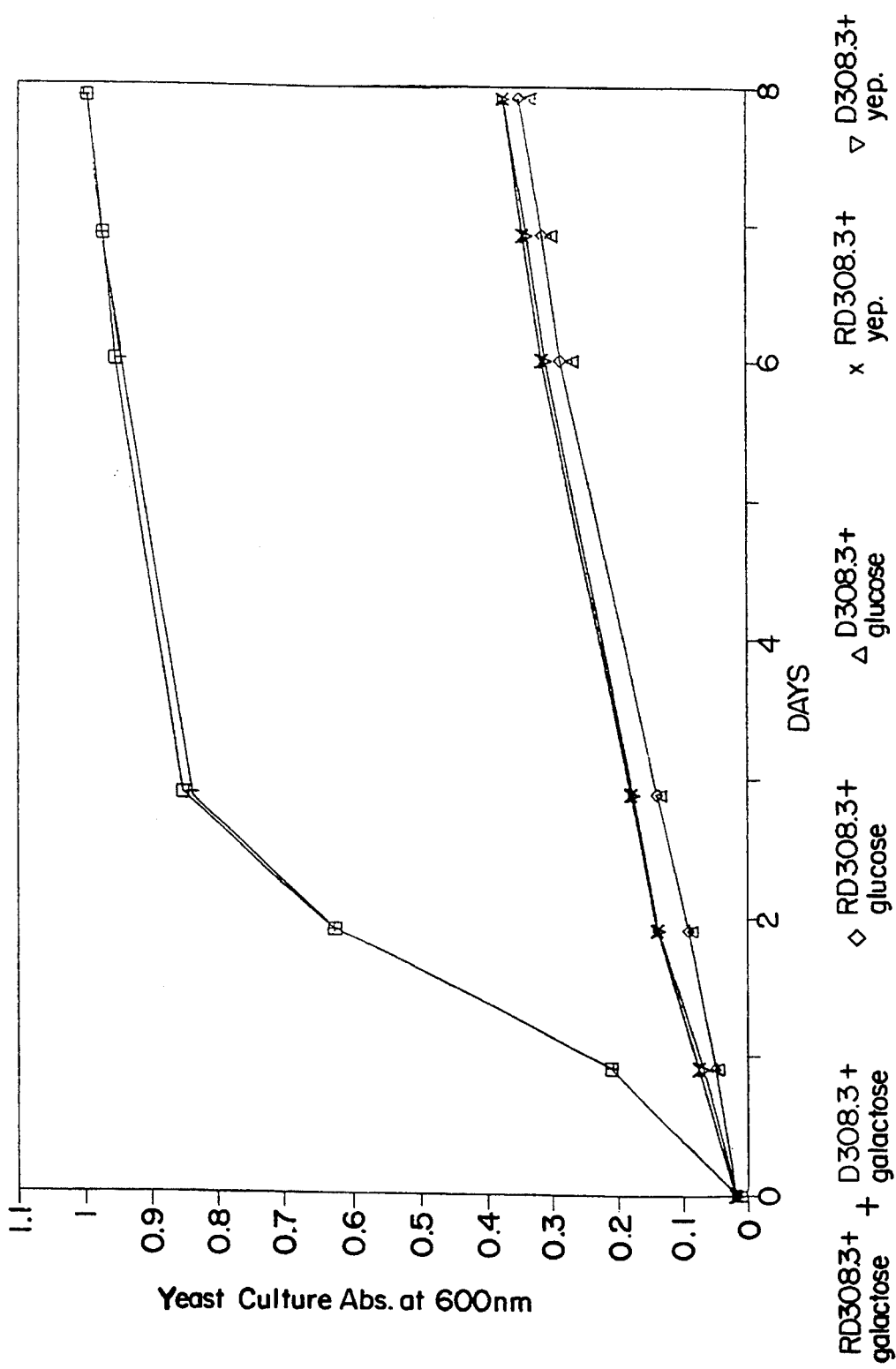
FIG. 10 depicts the growth of D308.3 and RD308.3 yeast on three different media as a function of absorbance.

The absorbance of each resulting sample was measured over time and is graphically illustrated in FIG. 10. The growth behavior of the D308.3 and RD308.3 yeasts appeared to be essentially the same for all three of these growth media. Furthermore, both of these yeasts appear able to readily metabolize galactose, but can only grow slightly on YEP or YEP/glucose. It is also interesting to note that both the D308.3 strain and the RD308.3 strain grew slightly less on the YEP/glucose than on YEP alone. This further demonstrates the substantial inability of these yeasts to metabolize glucose.

The auxotrophic markers adenine, histidine, methionine and tryptophan as growth supplements for the D308.3 and RD308.3 strains were compared by standard techniques. The D308.3 yeast was not able to grow on galactose minimal media unless all four of these growth supplements were present, but the RD308.3 yeast was able to grow if only the histidine, methionine and tryptophan were added.

Thus, the only significant difference noted between the auxotrophic markers of these two strains was that the D308.3 yeast requires adenine supplementation while the RD308.3 yeast does not. Accordingly, it is believed that the RD308.3 yeast will behave substantially as described above in connection with the D308.3 yeast when added to dough, but the slight discoloration of baked goods associated with doughs containing the D308.3 yeast should be substantially eliminated.

As noted above, a preferred embodiment of the invention provides a yeast which is substantially incapable of fermenting carbohydrates native to a flour but capable of fermenting a non-native carbohydrate. In a first particularly preferred embodiment, this yeast comprises a diploid yeast which is substantially incapable of fermenting carbohydrates native to wheat flour, but is capable of fermenting a non-native sugar such as galactose. This yeast is referred to herein as a diploid GAL+ yeast.

The GAL+ yeast described and tested in the above description is perfectly suitable for producing refrigeratable yeast-leavened doughs. In a commercial production setting, though, it may be desirable to provide such a yeast which is more stable and robust. In commercial operations, there is the possibility that the strain of yeast used in producing doughs could come into contact with other strains of yeast which are not GAL+. If the GAL+ yeast being used is a haploid, the possibility exists that the GAL+ yeast will mate with a contaminating strain of yeast, affecting the integrity of the yeast being used. Similarly, there is the possibility that some of the haploid GAL+ yeast strain may revert to the wild-type and become capable of freely metabolizing glucose or other carbohydrates native to the flour.

Some contamination of the yeast should not be problematic in commercial dough production. If the yeast strain becomes too contaminated, though, the yeast added to the dough composition may be capable of metabolizing native carbohydrates to an appreciable extent. This could yield yeasts which adapt to the carbohydrate profile in the dough being produced and continue to produce significant amounts of carbon dioxide even after the predetermined supply of the non-native carbohydrate is exhausted. This, in turn, could produce doughs having unacceptable rheology after extended shelf storage and could conceivably cause pressures high enough to cause the containers in which the dough is packaged for storage to rupture.

Accordingly, it is desirable to have a yeast which is less sensitive to contamination and less likely to revert to the glucose-utilizing wild type. It is believed that a diploid GAL+ yeast of the invention is more robust and less sensitive to contamination and less likely to revert to wild type.

EXAMPLE 7

In an attempt to provide a more robust yeast strain for use in commercial dough manufacturing operations, a diploid strain of GAL+ yeast was created. The D308.3 and RD308.3 strains are both mating type "α" haploid GAL+ yeasts and therefore cannot mate with one another to form a suitable diploid strain. A mating type "a" GAL+ yeast strain was therefore created to mate with either or both of the D308.3 and RD308.3 yeasts.

The following strains of yeast were used in creating the desired GAL+ diploid yeast:

| Strain | Genotype |
|--------|----------|
| XA83-5B | a lts8 lys2 leu1 |
| D308.3 (trp+) | α hxk1 hxk2 glk1 ade1 his2 met14* |
| RD308.3 | α hxk1 hxk2 glk1 trp1 his2 met14 |
| YM3270 | α zwf1:: URA3 ura3–52 his3–200 ade2–101 lys2–801 try1–501 |

The XA83-5B strain of yeast is available to the public from the YGSC under the same designation. The YM3270 was aquired from Dr. Mark Johnston of the Washington University University of Medicine in Saint Louis, Mo., U.S.A. These strains of yeast were found to be useful in the present mating protocol in that the XA83-5B yeast allowed the generation of a GAL+ haploid having a mating type a and the YM3270 yeast was useful in testing to confirm that the resultant yeast was indeed mating type a. It is believed and should be understood, though, that other yeasts having an a mating type could have been used instead. This is particularly true in the case of the YM3270 yeast, which was simply used to determine the mating type of a yeast generated as outlined below.

The D308.3 (trp+) yeast used in this experiment was a spontaneous revertant of the D308.3 yeast detailed above and available to the public from the ATCC under number ATCC 74211. The deposited D308.3 yeast was determined to need tryptophan supplementation in order to grow at a suitable rate. This D308.3 (trp+) yeast (also referred to below as D308.3' yeast) is a spontaneous revertant of the deposited D308.3 which does not require tryptophan supplementation for suitable growth. The D308.3' yeast was isolated in a manner analogous to the procedure outlined above in Example 6 for isolating the RD308.3 yeast. In particular, a concentrated paste of the D308.3 yeast was obtained and spread on a "tryptophan drop out" medium (i.e. a medium which does not contain any supplemental tryptophan) at a concentration on the order of about $1 \times 10^7$ to about $1 \times 10^8$ CFU/ml. The formula of the tryptophan drop out medium was substantially the same as that for the adenine drop out medium of Example 6, but the tryptophan in that formulation was replaced with adenine so that there was substantially no tryptophan in the medium.

These inoculated drop out plates were incubated and colonies of the yeast which grew on the drop out medium, and therefore must not require tryptophan supplementation for growth, were isolated. These isolated revertant strains were once again plated onto a tryptophan drop out medium and incubated and growing colonies were isolated from that plate. Samples of these isolated colonies were once again plated onto Tryptophan drop out medium, incubated and isolated one last time to remove substantially all non-revertant yeast from the isolated colonies. These isolated colonies are the D308.3' yeast used in the present Example 7.

The mating type a GAL+ haploid yeast was created by crossing the XA83-5B yeast, which is a mating type a yeast, and the RD308.3 yeast. The crossing was carried out under a protocol derived from *Methods in Yeast Genetics, A Laboratory Course Manual*, referred to and incorporated by reference above, at pp. 53–59, as follows:

XA83-5B yeast and RD308.3 yeast were plated onto separate YEP+galactose agar plates using a sterile loop to apply the strains on their respective plates in a series of parallel lines about 7 mm apart. These plates were allowed to incubate at approximately 30° C. for about 24 hours.

An impression of the mating type a XA83-5B strain was made on a replicate plate pad. This impression was imprinted onto a fresh plate including a YEP+galactose medium (about 1 wt. % bacto-yeast extract, about 2 wt. % bacto-peptone, about 2 wt. % bacto agar, and about 2 wt. % galactose, with the balance being distilled water). Using a fresh replicate plate pad, an impression of the mating type α RD308.3 strain was made. The second replicate pad was imprinted on the same YEP+galactose plate used for the previous imprinting, but at an orientation generally perpendicular to the first imprint, resulting in a pattern of yeast strains resembling a checkerboard. This doubly imprinted YEP+galactose plate was incubated at approximately 30° C. for about 24 hours.

The YEP+galactose plate thus prepared was imprinted on a synthetic dextrose minimal media plate. The synthetic dextrose minimal media included about 6.7 g of bacto-yeast nitrogen base without amino acids, about 20 g of bacto-agar and about 20 g of glucose in about 1 liter of distilled water. Such a minimal medium is taught in *Methods in Yeast Genetics, A Laboratory Course Manual*, noted above, at pp. 178–179. These synthetic dextrose minimal media plates were incubated for about 24 hours at about 30° C.

Growth at the intersections of the "checkerboard" pattern was scored and plated onto a fresh synthetic dextrose minimal media plate to isolate the diploid (crossed) colonies from the haploid colonies. The diploid colonies isolated on the synthetic dextrose minimal media plate were streaked onto a plate of sporulation media and incubated for about 4–5 days at about 30° C. The sporulation media contained about 10 g (1 wt. %) potassium acetate, about 1.0 g (0.1 wt. %) bacto-yeast extract, about 0.5 g (0.05 wt. %) galactose, about 20 g (2.0 wt. %) bacto-agar, with the balance being about 1000 ml distilled water.

About one loopful of yeast cells was taken from the sporulation plate and combined with about 300 microliters distilled water and approximately 15 microliters glusulase in an Eppendorf™ microfuge tube. This solution was mixed by vortex and incubated at about 30° C. for approximately 30 minutes. The incubated sample was briefly sonicated to separate spore clusters. Serial dilutions of about $10^{-4}$, $10^{-5}$ and $10^{-6}$ of the sonicated sample were plated onto YEP+ galactose glass petri plates.

These serial dilutions were then exposed to ethyl ether fumes in a manner adapted from "Guide to Yeast Genetics and Molecular Biology", Guthrie and Fink editors, in *Methods of Enzymology*, vol. 194, pp. 146–147 (1991), the teachings of which are incorporated herein by reference. In this process, a 4 mm×4 mm piece of filter paper was placed into the inverted lid of each petri dish containing one of the serial dilutions. In a ventilated hood, 0.75 ml of ethyl ether was added to each filter paper and the lids and dilutions were placed in a glass chamber along with a beaker containing 10 ml of ethyl ether to maintain the vapor pressure in the chamber elevated.

The chamber was sealed and the samples were incubated for about 15 minutes at room temperature, at which time an additional 0.75 ml portion of ethyl ether was added to each falter paper square. These samples were again incubated in the glass chamber at room temperature for about 15 minutes, following which the samples were removed from the chamber and allowed to sit in the open atmosphere with the lid of each sample ajar for about 30 minutes.

Some 287 putative haploid GAL+ yeast colonies were isolated from these $10^{-4}$, $10^{-5}$ and $10^{-6}$ dilution plates. Each of these putative haploids were grid plated onto YEP+ galactose plates and onto YEP+glucose plates and incubated at about 30° C. for approximately 48 hours to determine which of the isolated putative XA83-5B x RD308.3 strains were able to grow on the galactose-enriched medium but not the glucose-containing medium. 50 of these 287 colonies were determined to be GAL+ by their ability to grow well on galactose but general inability to grow on glucose. These GAL+ haploids were then isolated by streaking them onto fresh YEP+galactose plates.

The mating type of each of these 50 GAL+ haploids was determined by attempting to mate samples of these yeasts with the YM3270 yeast noted above. Since the YM3270 yeast is mating type α, only mating type a strains of the isolated GAL+ yeasts will be able to mate with the YM3270 yeast. This therefore identifies those GAL+ strains capable of mating with the D308.3' and RD308.3 yeasts, both of which are mating type α, to produce the desired diploid of the invention.

In determining ability to mate, the procedure utilized was analogous to the mating procedure, outlined above, used to cross the RD308.3 and XA83-5B strains. In mating the isolated GAL+ strains and the YM3270 yeast, three generally parallel lines of each of three different strains of the GAL+ yeasts were streaked onto a single YEP+galactose petri dish (for a total of nine streaks per petri dish). A number of such petri dishes were prepared so that samples of each of the isolated GAL+ strains were plated onto a petri dish. On a separate plate, six generally parallel lines of the YM3270 yeast were streaked onto YEP+galactose medium. Both the GAL+ samples and the YM3270 plate were incubated at about 30° C. for about 24 hours.

The GAL+ strains and the YM3270 strain were replica plated onto a series of plates in a generally perpendicular orientation to yield a checkerboard pattern, as outlined above in the earlier mating protocol. These strains were plated onto synthetic dextrose complete uracil dropout media rather than the synthetic dextrose minimal media utilized in the earlier mating. The synthetic dextrose complete uracil dropout media contained about 6.7 g of a bacto-yeast nitrogen base substantially without amino acids, about 20 g of glucose, about 20 g of bacto-agar, and about 2 g of a "drop out mix", with the balance being about 1000 ml of distilled water. The "drop out mix" contained about 0.5 g of adenine, about 4.0 g of leucine, about 0.2 g of para-aminobenzoic acid, and about 2.0 g of each of alanine, arginine, asparagine, aspartic acid, cysteine, glutamine, glutamic acid, glycine, histidine, inositol, isoleucine, lysine, methionine, phenylalanine, proline, serine, threonine, tryptophan, tyrosine and valine.

These checkerboard plates were incubated at about 30° C. for about 24 hours and scored for growth. Since the YM3270 yeast strain has been determined to require uracil supplementation for growth, plating the yeast onto the uracil drop out medium effectively permits mated diploid yeasts to be separated from the haploid colonies. Of the 50 isolated GAL+ colonies, only six were found to be viable haploid strains of mating type a based on their ability to mate with mating type α YM3270 yeast via auxotrophic complementation on the uracil dropout media.

The auxotrophic markers of the six GAL+ strains identified as being mating type a and the D308.3' and RD308.3 strains were then determined using known techniques. In particular, samples of each of these six strains were plated onto a series of plates having different media. The media for all of the plates included about 6.7 g of a bacto-yeast nitrogen base substantially without amino acids, about 20 g of glucose, about 20 g of bacto-agar, and about 2 g of a "drop out mix", with the balance being about 1000 ml of distilled water. The general formula of the "drop out mix" was about 0.5 g of adenine, about 4.0 g of leucine, about 0.2 g of para-aminobenzoic acid, and about 2.0 g of each of alanine, arginine, asparagine, aspartic acid, cysteine, glutamine, glutamic acid, glycine, histidine, inositol, isoleucine, lysine, methionine, phenylalanine, proline, serine, threonine, tryptophan, tyrosine, uracil and valine.

The media formulations differed from one another in that each "drop out mix" added to the medium omitted one of isoleucine, tryptophan, lysine, adenine, histidine, or methionine, but included all of the other ingredients of the formula. These series of plates were incubated at about 30° C. for about 24 hours and visually inspected for growth. Although drop-out media were used in this protocol, it should be understood that any recognized means for determining auxotrophic markers could have been used. The following auxotrophic markers were determined for each of the six mating type a GAL+ strains:

| Yeast Strain | Drop Out Media | | | | | |
|---|---|---|---|---|---|---|
| | ade | met | his | lys | leu | trp |
| a GAL+ #6 | − | + | − | − | + | + |
| a GAL+ #11 | + | +/− | + | + | + | − |
| a GAL+ #33 | + | − | − | − | + | + |
| a GAL+ #44 | + | +/− | − | + | − | + |
| a GAL+ #46 | − | +/− | − | + | + | + |
| a GAL+ #50 | − | + | − | + | + | − |

In this table, a "+" designation indicates that the strain grew on the identified drop out media, a "−" designation indicates that the strain did not appear to grow well on the identified drop out media, and a "+" designation indicates that this strain appeared to grow on the identified drop out media but required the addition of met when mated to strains of either RD308.3 or D308.3' via auxotrophic complementation as outlined below.

Based on these auxotrophic determinations, mating type a GAL+ strain numbers 6, 33, 44, 46 and 50 were mated to parent strain RD308.3 while mating type a GAL+ strain number 11 was mated to strain D308.3'. Substantially the same mating protocol as that outlined above for mating the RD308.3 and XA83-5B strains was used in mating the present strains. However, in this mating protocol, the synthetic galactose minimal media used to isolate the resulting diploid colonies from their parent haploids were supplemented with amino acids as follows:

| Mating Pair | Synthetic Galactose Minimal Media Amino Acid Supplement(s) |
|---|---|
| α RD308.3 × a GAL+ #6 | his |
| α D308.3' × a GAL+ #11 | met* |
| α RD308.3 × a GAL+ #33 | his, met |
| α RD308.3 × a GAL+ #44 | his, met* |
| α RD308.3 × a GAL+ #46 | his, met* |
| α RD308.3 × a GAL+ #50 | his, trp |

*diploids appeared to require met supplementation for growth although the strain was seemingly heterozygous with respect to the met-requiring mutation.

Each of these six diploid strains were tested to see if they did indeed remain GAL + in the sense that they were able to grow on galaclose but were substantially unable to grow on glucose. A heavy inoculum (e.g. on the order of about $10^7$ CFU/ml) of each diploid and the RD308.3 and D308.3' strains were plated onto a YEP+galactose plate and a YEP+glucose plate. All six of the diploids and both the RD308.3 and D308.3' haploids grew well on the galactose medium but did not exhibit any significant growth on the glucose medium.

Given the present disclosure, those skilled in the art can clearly make a GAL+ diploid yeast of the invention. It should be understood that the experimental procedure outlined above is just one of a wide variety of possible methods of accomplishing this end and other effective means for making GAL+ diploids of the invention will be obvious to those skilled in the art in light of the present teaching. For instance, one could select other starting yeasts than those used in the present example, the mating of yeast strains may be conducted in other known manners, and auxotrophic markers could be determined by other known means.

It is believed that the diploid GAL+ yeast strain of the present invention will be both more active and more resistant to reversion and contamination than either of the RD308.3 and D308.3' haploid strains. Such improved activity and resistance should yield a GAL+ yeast strain which is more valuable in commercial dough manufacturing operations than either the RD308.3 or D308.3' haploid yeasts.

EXAMPLE 8

The properties of the GAL+ diploids produced in Example 7 relevant to use of the yeast in leavening refrigeratable dough in accordance with the invention were tested. The genotypes of the six GAL+ diploids produced in Example 7, as well as those of the RD308.3 and D308.3' strains, are believed to be as follows, based on the genotypes of the parent strains:

| Yeast Strain | Genotype |
|---|---|
| a/α GAL+ #6 | a/α hxk1/hxk1, hxk2/hxk2, glk1/glk1, his2/his2 |
| a/α GAL+ #11 | a/α hxk1/hxk1, hxk2/hxk2, glk1/glk1, met14/met14 |
| a/α GAL+ #33 | a/α hxk1/hxk1, hxk2/hxk2, glk1/glk1, met14/met14, his2/his2 |
| a/α GAL+ #44 | a/α hxk1/hxk1, hxk2/hxk2, glk1/glk1, met14/met14, his2/his2 |
| a/α GAL+ #46 | a/α hxk1/hxk1, hxk2/hxk2, glk1/glk1, met14/met14, his2/his2 |
| a/α GAL+ #50 | a/α hxk1/hxk1, hxk2/hxk2, glk1/glk1, his2/his2, trp5/trp5 |
| α RD308.3 | α hxk1 hxk2 glk1 trp5 his2 met14 |
| α D308.3' | α hxk1 hxk2 glk1 his2 met14 |

First, the ability of each of the above-listed strains of yeast to utilize certain carbohydrates was tested. One loop of each yeast strain was added to a separate 300 ml flask containing about 50 ml of YEP+ galactose liquid media having about the same formula as outlined above. These flasks were incubated at about 30° C. for about 18 hours while being shaken. Three 10 ml test tubes for each of the incubated samples were provided with about 100 μl of the incubated sample, with one test tube for each sample containing about 5 ml YEP, another test tube containing about 5 ml YEP+dextrose and the third test tube containing about 5 ml YEP+galactose. The formulas of these media were also substantially the same as set forth above for like media. A set of three control test tubes was prepared by placing about 5 ml of YEP, YEP+dextrose or YEP+galactose in each of three test tubes without any added yeast.

The absorbency of each of these resulting test tubes was measured at 600 nm prior to and during incubation at about 30° C. The absorbance of the test tubes containing YEP or YEP+dextrose media were measured over a period of about two weeks while the absorbance of the test tubes containing YEP+galactose was measured for about 100 hours of incubation both with shaking and without shaking of the test tubes.

It was found that each of the diploid a/α GAL+ strains except a/α GAL+ #50 grew noticeably more quickly than the RD308.3 yeast strain on the galactose medium. The D308.3', RD308.3 and a/α GAL+ strain numbers 6, 11, 33 and 44 grew rather poorly on both YEP and YEP+glucose media. The a/α GAL+ #50 yeast strain grew well on the galactose medium, but not appreciably better than the RD308.3 strain. The a/α GAL+ #44 and a/α GAL+ #50 strains also appeared to begin growing in the YEP+glucose medium after about 12 days of incubation. Although the reason for this apparent ability to utilize glucose is not clearly understood, it has been surmised that either these strains spontaneously reverted to glucose utilization or the samples used in the test were contaminated with another organism.

The ability of the six diploid a/α GAL+ strains to revert to glucose utilization was tested by first adding a loop of the yeast strains to separate 10 ml volumes of YEP+galactose and incubating these samples at about 30° C. for about 20 hours while shaking. Three separate YEP+glucose plates for each sample were prepared by spread plating 100 µl of the sample on each of the sample's three plates. In addition, $10^{-4}$, $10^{-5}$ and $10^{-6}$ serial dilutions of each sample were spread plated onto similar YEP+galactose plates.

These plates were incubated and the number of observed revertant colonies for each of the six strains on their respective YEP+glucose plates were recorded. These rates were then compared to the total number of actual colonies plated onto the plates by comparison to the serial dilutions on the YEP+galactose plates. This technique for determining reversion frequency is well know in the art. The reversion rates of these samples was so determined to be as follows:

| Yeast Strain | Reversion Frequency (# of revertants per $10^6$ CFU) |
| --- | --- |
| a/α GAL+ #6 | 0.10 |
| a/α GAL+ #11 | 0.04 |
| a/α GAL+ #33 | 0.03 |
| a/α GAL+ #44 | 0.03 |
| a/α GAL+ #46 | 0.09 |
| a/α GAL+ #50 | 0.01 |
| α RD308.3 | 0.23 |

Thus, the frequency with which the diploid yeast strains of the invention reverted to glucose utilization was significantly lower than the reversion frequency of the parent RD308.3 haploid. Accordingly, it appears as though the diploid yeasts of the invention are probably more stable than the RD308.3 yeast of the invention, at least with respect to reversion to glucose utilization.

These diploid strains were evaluated in dough systems to determine their utility in leavening a refrigeratable dough in accordance with the invention. First, the yeast strains were grown by inoculating 300 ml culture flasks containing about 50 ml YEP+galactose liquid media with one isolated yeast colony, with two such inoculated flasks being prepared for each strain of yeast. These flasks were incubated at about 30° C. for about 48 hours while shaking the flasks. These incubated samples were then added to separate 2 liter flasks containing about 1000 ml YEP+galactose liquid media and the larger flasks were incubated at about 30° C. for about 24 hours prior to being harvested in paste form as outlined above in Example 2.

A dough was prepared from each strain of the diploid yeasts as well as the RD308.3 yeast. Each dough contained: about 758 g (56.1 wt %) wheat flour, about 49.0 g (3.5 wt %) wheat gluten preblend, about 498 g (35.6 wt %) water, about 14 g (1.0 wt %) salt, 35 g (2.5 wt %) of the yeast paste, about 14 g (1.0 wt %) galactose and about 4.2 g (0.3 wt %) yeast food. The yeast food used in this formula is commercially available from Red Star Universal Foods Corporation of Milwaukee, Wis., USA under the designation "Regular Yeast Food". The water, galactose and yeast food were combined and mixed with the yeast paste in a McDuffy™ mixing bowl at speed 1 for about 30 seconds, followed by mixing at speed 2 for about 6 minutes.

50-gram samples of the doughs so produced were placed into a Risograph™ sample jar and gas evolution data was collected for the samples as they were incubated at about 30° C. for about 42 hours. The 50 g dough samples leavened with diploid strain numbers 33, 46 and 50 and the sample leavened with the RD308.3 yeast each generated about 90–100 ml of $CO_2$ over the course of the test, which is within the 100–200 ml $CO_2$/100 g of dough deemed necessary to properly proof the dough. The sample leavened with the a/α GAL+ #44 yeast generated only about 65 ml $CO_2$.

The diploid strain numbers 33 and 46 appeared to generate $CO_2$ a little more rapidly than the haploid RD308.3 yeast. Diploid strain numbers 6 and 11 generated gas at a lower rate than the RD308.3, but the reason for this lower rate is not understood at this time in light of the liquid culture testing. The #44 and #50 strains appeared to generate gas slightly more slowly than the haploid parent strain.

The dough remaining after the Risograph samples were taken was rolled into sheets about one quarter of an inch thick and cut into rectangular slabs weighing about 250 g. These slabs were rolled into a log shape and placed into standard, 250 g-capacity spirally wound dough cans. Similar slabs of a standard chemically leavened dough such as is used in current commercial refrigerated dough operations was also placed into such cans. The canned doughs were proofed at about 100° F. (about 38° C.) until pressure in the can reached about 15–20 psi. These proofed dough samples were then storm in the cans at about 4° C. and the internal pressure of the cans was monitored over time.

The dough leavened with RD308.3 yeast took about three hours to proof within the can to the desired degree. All of the doughs leavened with the diploid yeasts, with the exception of the a/α GAL+ #6 yeast, proofed somewhat more quickly than the RD308.3 dough, with the dough containing a/α GAL+ #33 taking only about 2.5 hours and the dough leavened with the a/α GAL+ #46 taking only about two and a quarter hours. The a/α GAL+ #6 yeast-leavened dough took significantly longer, with a proof time of over 5 hours.

Figure 11:
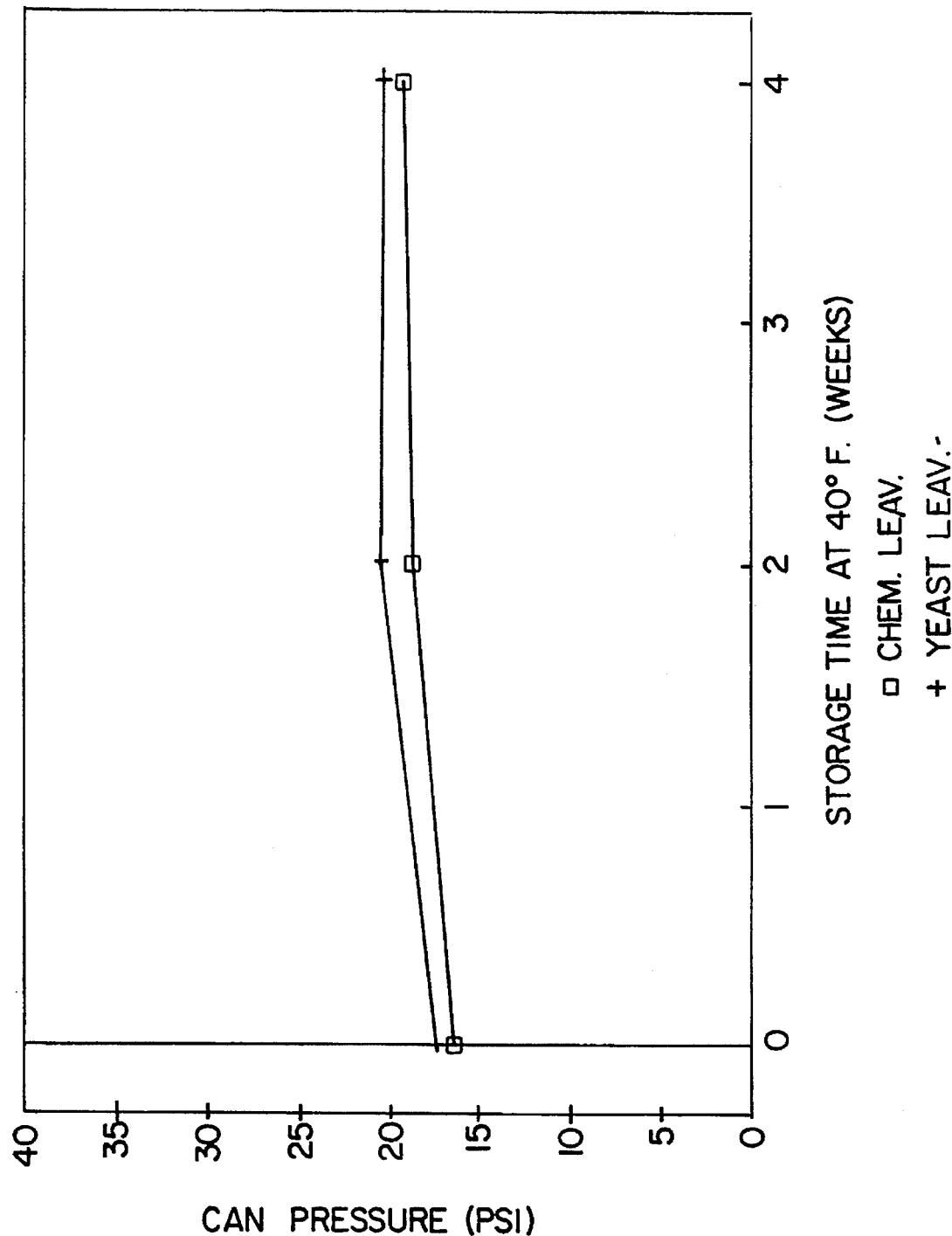
FIG. 11 depicts measured can pressure as a function of time for doughs leavened with diploid GAL+ yeast of the invention.

FIG. 11 is a plot of the measured pressures in canned dough samples as a function of time. The upper line illustrates the can pressures for the sample leavened with the a/α GAL+ #33 yeast, while the lower line (having data points illustrated by hollow boxes) represents measured pressures for the chemically leavened dough sample. Measurements of can pressure for both of the samples were started after the dough was proofed in the cans, so the initial internal pressure is between 15 and 20 psi for both samples.

The pressure in both cans remained substantially constant over the month-long time period illustrated in FIG. 11 and the behavior of the dough leavened with the yeast of the invention compares favorably with that of the chemically leavened sample. Since the plots of both of these samples remained generally flat over the four weeks during which measurements were collected, there is no reason to believe that the pressures in the containers would reach any critical stage within the anticipated 90-day shelf life of commercial refrigerated doughs. Hence, it appears that the diploid GAL+ yeast of the present invention is well suited for making doughs which can be stored at refrigeration temperatures for extended periods of time.

As noted above, a yeast according to a further embodiment of the invention is both substantially incapable of fermenting carbohydrates native to wheat flour and low temperature sensitive. As explained in co-pending application Ser. No. 07/829,453, now abandoned, the teachings of which were incorporated by reference above, low temperature sensitive yeasts ("lts" yeasts) are characterized by the fact that they behave essentially "normally" at elevated temperatures but become essentially dormant or inactive at refrigeration temperatures.

In producing a GAL+/lts yeast of the invention, a GAL+ yeast of the invention as outlined above and a low temperature sensitive yeast are mated to produce a GAL+/lts yeast. Low temperature sensitive yeasts desirably comprise genetic mutations of normal strains of yeast. Normal strains of yeast are believed to contain a certain percentage of such yeast cells, and these lts mutants of the yeast may be isolated in any of a variety of methods.

For instance, cold sensitive mutants of the yeast may be isolated by tritium suicide enrichment as described by Littlewood and Davies in "Enrichment for Temperature Sensitive and Auxotrophic Mutants in *Saccharomyces cerevisiae* by Tritium Suicide", *Mutat. Res.* Vol. 17, pp. 315–322 (1973), the teachings of which are incorporated herein by reference. In this tritium suicide enrichment process, a strain of yeast, which is preferably *S. cerevisiae,* is placed in a growth medium at normal temperatures and the temperature is then reduced to refrigeration temperatures. Once the yeast has reached the lower temperature, tritiated uridine or tritiated amino acids may be supplied to the culture. Those cells which continue to remain active at these lower temperatures incorporate these precursors and are killed off by the tritium. Low temperature sensitive mutants present in the yeast sample, though, will not incorporate the uridine or the amino acids because they remain substantially inactive at the lower temperature. Accordingly, the lts mutants preferentially survive the reduced temperature storage.

Some researchers in the field of genetics have investigated certain properties of these yeasts. For instance, Ursic and Davies reported the results of certain studies in "A Cold-Sensitive Mutant of Saccharomyces cerevisiae Defective in Ribosome Processing", *Molec. Gen. Genet.* 175,313–323 (1979), and Singh and Manney discuss the results of their testing in "Genetic Analysis of Mutations Affecting Growth of *Saccharomyces cerevisiae* at Low Temperature", *Genetics,* 77:651–659 (August 1974); the teachings of these articles are incorporated herein by reference.

There appear to be a relatively large number of genes in yeast which can mutate to prevent the growth of the yeast at low temperatures. For purposes of the present invention, though, it does not appear to be critical which of these genes is affected in the mutant which is utilized. The important factor in selecting a yeast is that the yeast should remain active at elevated temperatures, such as room temperature, yet become substantially inactive and substantially cease carbon dioxide production at refrigeration temperatures. Eight suitable examples of such lts yeasts are available from the ATCC under deposit numbers ATCC 74124 through ATCC 74131.

The substantial inactivity of the lts yeast at refrigeration temperatures permits one to predictably proof or leaven the dough to the desired degree at elevated temperatures, then hold the leavened dough at refrigeration temperatures for extended periods of time. Such extended storage will not significantly change the volume of the lts yeast-leavened dough because the yeast is inactive and does not generate any significant volume of additional carbon dioxide. This allows a commercial dough manufacturer to controllably leaven or proof dough and place it in a sealed container for sale to consumers at a later date. So long as the dough is stored at refrigeration temperatures until it is sold, the pressure in the container should not substantially increase over time. Even if the dough is temporarily warmed above refrigeration temperatures, as during improper transportation or storage, if it is chilled back down, leavening action brought on by the elevated temperatures should be arrested and the yeast should once again become inactive.

GAL+/lts yeasts of the invention are believed to be superior to at least the haploid GAL+ strain explained in detail above for use in a refrigerated dough system. The low temperature sensitive characteristics of the GAL+/lts yeast provides a back-up mechanism for limiting excess carbon dioxide production if the strain does become contaminated. More particularly, it is believed that the low temperature sensitive nature of the yeast will render the yeast substantially inactive at refrigeration temperatures even if the yeast would otherwise continue to produce carbon dioxide.

For example, if some of the yeast reverts and more readily utilizes glucose, the low temperature sensitive nature of the yeast should limit any adverse effects from this contamination by substantially halting carbon dioxide when a dough leavened with this yeast is stored at refrigeration temperatures. Alternatively, if the integrity of the yeast strain is not compromised but an excess of a fermentable substrate (e.g. excess galactose) is inadvertently used in the dough composition, GAL+/lts yeast should substantially cease carbon dioxide production during refrigerated storage of the dough even though excess fermentable substrate may still be present.

EXAMPLE 9

In example 7, yeast strain XA83-5B was mated with yeast strain RD308.3 to produce diploid yeasts. While yeast strain RD308.3 is a GAL+ yeast, it has been previously determined that the XA83-5B yeast is a low temperature sensitive strain.

As noted above in Example 7, of the 287 putative GAL+ haploid yeast colonies isolated from the serial dilution plates, 50 strains were actually identified as GAL+ by their ability to grow on galactose-enriched medium, but substantially unable to grow on the glucose-containing medium. In Example 7, six of these strains determined to be mating type α were mated with parent strain RD308.3 or strain D308.3'.

In the present experiment, one loop of each of the fifty isolated GAL+ haploids of Example 7 were added to separate 10 ml sterile test tubes containing about 5 ml YEP+ galactose. These inoculated samples were incubated at about 30° C. while shaking for about 24 hours to grow the strains. Two samples (about 100 µl per sample) of each of these 24-hour incubated specimens were then used to inoculate separate sterile 10 ml test tubes containing about 5 ml of YEP+galactose. This yielded 50 pairs of inoculated test tubes.

One inoculated test tube from each pair was incubated at about 30° C. while the other test tube from each pair was incubated at about 12° C. Absorbance measurements at about 600 nm were taken for each of the test tubes incubated at 30° C. for several days (i.e. until all of the samples appeared to reach log phase). Absorbance of the samples incubated at 12° C. at about 600 nm was also measured, with measurements being taken after about 10 and about 30 days of incubation.

All of the yeast strains appeared to grow well, as indicated by the rate of increase in absorbance, when incubated at about 30° C. Of the 50 GAL+ yeast strains tested, though, five strains appeared to be able to grow poorly or not at all, as indicated by little or no appreciable increase in absorbance, when incubated at about 12° C. These five strains therefore appear to be low temperature sensitive, as that term is used herein. These apparent GAL+/lts strains were assigned the designations GAL+/lts #8, GAL+/lts #17, GAL+/lts #21, GAL+/lts #26 and GAL+/lts #48.

In order to confirm the low temperature sensitivity of these five strains of yeast, the growth rates of colonies of these yeasts at 30° C. and 12° C. were compared to the parent RD308.3 and XA83-5B strains. Seven generally parallel rows, each row having four colonies of one of these seven strains, were grid plated onto duplicate YEP+galactose agar plates. In forming the rows, sterile tooth picks were used to transfer a colony of the yeast. Two such plates were made and one plate was incubated at about 30° C. while the other was incubated at about 12° C.

Figure 12:
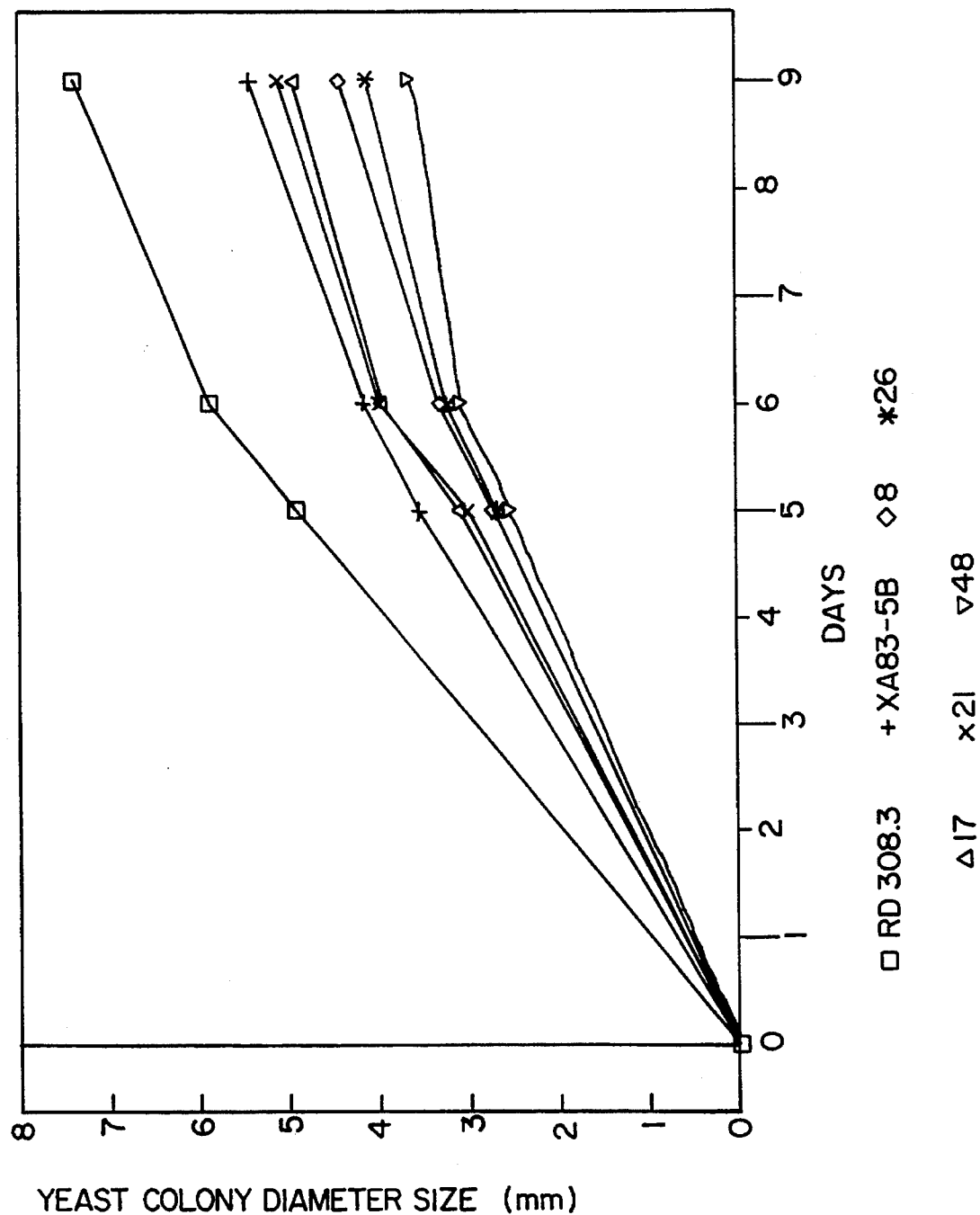
FIG. 12 depicts colony size for GAL+/lts yeast strains of the invention as a function of time at about 30° C.
Figure 13:
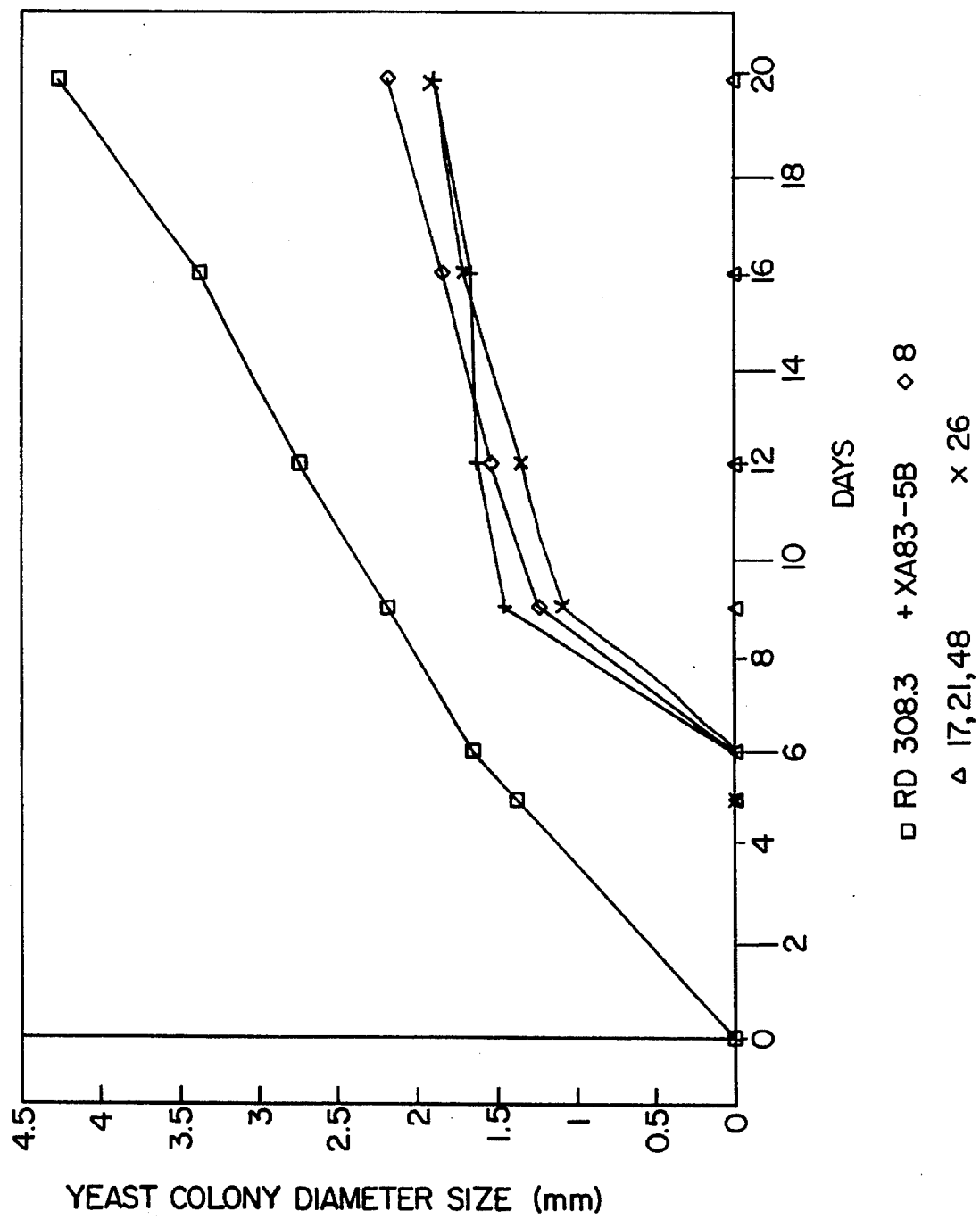
FIG. 13 depicts colony size for GAL+/lts yeast strains of the invention as a function of time at about 12° C.

The colonies resulting frown this plating had an initial diameter about equal to that of the tooth pick with which they were transferred and measurements of the diameters of the colonies on the two differently incubated plates were measured over time. FIGS. 12 and 13 illustrate the colony diameter data of yeast strains GAL+/lts #8, GAL+/lts #17, GAL+/lts #21, GAL+/lts #26, GAL+/lts #48, RD308.3 and XA83-5B for the plate incubated at about 30° C. and the plate incubated at about 12° C., respectively.

The diameters were measured visually with a digital micrometer and, since the tooth pick used to transfer the samples created a slight indentation in the agar plates, it was rather difficult to obtain reliable measurements below about 1.0 mm in diameter. Measurements for all four of the colonies one the row dedicated to one strain of yeast were averaged together to yield the measurements shown in these two graphs.

FIG. 12 shows that all six of the illustrated strains of the yeast grew reasonably well over the course of the test, with colonies ranging from about 3.5 mm to about 7.5 mm by the end of about 9 days of incubation at about 30° C. The RD308.3 yeast grew the most rapidly while all of the low temperature strains grew a little more slowly. The GAL+/lts #21 and GAL+/lts #17 strains grew at about the same rate as the XA83-5B yeast, with the GAL+/lts #8 and GAL+/lts #48 strains growing a little more slowly.

FIG. 13 represents the growth rates of the same yeasts at about 12° C. The growth rate of the RD308.3 yeast was slower than that illustrated in FIG. 12 for 30° C. incubation, but this strain of yeast nonetheless seemed to grow fairly well at the lower temperature. The XA83-5B yeast and the GAL +/lts #8 and GAL+/lts #26 strains all showed some measurable growth over the 20-day test, but the maximum colony size for any of these three yeasts was still no more than about 2 mm. There appears to be a rather sudden jump in colony diameter after about a week of incubation, but as noted above, it was relatively difficult to read colony diameters accurately below about 1.0 mm. It is believed that these colonies grew at a relatively steady, though quite slow, rate rather than experiencing a sudden growth spurt between 6 days incubation and the next measurement after about 9 days of incubation.

It is believed that the 12° C. temperature at which these yeasts were incubated is about at the upper limit of the XA83-5B yeast strain's low temperature sensitivity threshold and this might explain the slight, but measurable, growth of this strain at 12° C.

The other three strains of the GAL+/lts yeast of the invention, though, did not exhibit any measured growth when incubated at 12° C. This indicates that the GAL+/lts #17, GAL+/lts #21 and GAL+/lts #48 yeasts are, surprisingly, even more low-temperature sensitive than the XA83-5B parent strain. These three strains of the yeast also grew about as well as their low temperature sensitive parent at about 30° C.

Given that these strains of yeast also appear to be substantially unable to ferment any carbohydrates native to wheat flour, it appears that the GAL+/lts #17, GAL+/lts #21 and GAL+/lts #48 yeasts are particularly well suited for use in a refrigeratable dough composition of the invention. Accordingly, based on the evaluation outlined above, these strains would be the most preferred strains of those obtained by the present mating.

The present disclosure teaches how to select or isolate GAL+ and lts strains of yeast, at least one method of mating such yeasts, and methods for testing the resultant strains of yeast to isolate and evaluate GAL+/lts strains so obtained. Given the present teaching, it is well within the ability of one skilled in the art to make and test any number of GAL+/lts yeasts.

Another embodiment of the present invention provides a method of forming a dough which can be stored at refrigeration temperatures for extended periods of time without generating significant volumes of carbon dioxide. This method may further include the steps of packaging the dough, proofing the dough in the package, and storing the dough for an extended period of time at refrigeration temperatures.

In making a dough of the invention, flour, water, a yeast substantially incapable of fermenting carbohydrates native to the flour, and a quantity of a carbohydrate fermentable by the yeast are mixed together, as outlined above. The amount of the fermentable carbohydrate added to the dough is desirably sufficient to provide only the necessary degree of proofing of the dough; adding too much fermentable substrate could cause adverse changes in dough rheology due to overfermentation. This amount is optimally determined on a case-by-case basis for a given strain of yeast as different strains of yeast may utilize the fermentable substrate more efficiently than others. If so desired, additional flavoring ingredients, such as salt, additional quantities of sugars native to the flour, or wheat gluten, could be added to the dough to achieve a desired flavor in the final baked good produced from the dough.

In a particularly preferred embodiment of the method of the invention, the yeast used in making the dough is a GAL+ yeast and a predetermined quantity of galactose is added to the dough to provide the desired degree of proofing. This GAL+ may be the D308.3, D308.3' yeast or the RD308.3 yeast described above, but it is to be understood that other GAL+ yeasts can be made in accordance with the present disclosure which will also work in accordance with the invention.

As noted above, the method may further include the steps of packaging the dough, proofing the dough in the container, and storing the dough at refrigeration temperatures for an extended period of time. Virtually any known refrigeratable dough package known in the art may be used in this method. For instance, spirally wound dough containers such as those currently used in commercially manufactured refrigeratable dough products should suffice. A quantity of dough somewhat less than that necessary to fill the container is placed in the container, leaving a headspace in the container when it is sealed.

The dough may then be proofed in the container, expanding to fill the container and flush out any air in the headspace. The proofing is continued until substantially all of the fermentable carbohydrate is consumed by the yeast, at which point an internal pressure of about 15 to about 20 psi is attained in the container. This proofing may be advantageously carried out at an elevated temperature, e.g. about 30° C. to about 40° C., to allow the yeast to ferment, and thus proof the dough, more rapidly.

This proofed dough may then be placed in refrigerated storage for extended periods of time, desirably up to at least about two weeks. The dough of the invention is optimally capable of storage at refrigeration temperatures for at least about 90 days, the anticipated shelf life of current doughs, as explained above. By "refrigerated storage", storage at temperatures between about 12° C. and about 0° C., and preferably between about 4° and about 7.2° C., is intended.

Such temperatures are referred to in the present specification as "refrigeration temperatures".

While preferred embodiments of the present invention have been described, it should be understood that various changes, adaptations and modifications may be made therein without departing from the spirit of the invention and the scope of the appended claims.

What is claimed is:

1. A diploid yeast capable of fermentation in a medium that includes carbohydrates native to wheat flour without adenine supplementation provided carbohydrates with galactose are also in the medium.

2. A diploid yeast capable of fermentation in a medium that includes carbohydrates native to wheat flour without adenine supplementation provided carbohydrates with galactose are also in the medium, the diploid yeast being substantially inactive at temperatures between about 0° C. and 12° C.

3. The yeast of claim 2 wherein the yeast become substantially inactive at temperatures between about 4° C. and about 7.2° C.

4. The diploid yeast of claim 2 comprising a genotype free of genes for effectively synthesizing P1 hexokinase, P2 hexokinase and glucokinase.

5. A refrigeratable dough composition free of discoloration comprising wheat flour, water and diploid yeast, the diploid yeast capable of fermentation of the refrigeratable dough provided carbohydrates with galactose are also in the refrigeratable dough and being substantially inactive at temperatures between about 0° C. and 12° C.

6. A yeast strain deposited with the American Type Culture Collection under ATCC No. 74212 characterized by a capability of fermenting galactose as a sole carbohydrate source without adenine supplementation in a presence of carbohydrates native to wheat flour.

* * * * *

UNITED STATES PATENT AND TRADEMARK OFFICE
CERTIFICATE OF CORRECTION

PATENT NO. : 5,494,686
DATED : February 27, 1996
INVENTOR(S) : DAVID J. DOMINGUES It is certified that error appears in the above-indentified patent and that said Letters Patent is hereby corrected as shown below:

Col 1, line 5, delete the extra "space" between the number "199" and "1";

Col. 9, line 12, delete the "." after the word "evolution";

Col 11, line 40, delete the word "When" and insert the word --when--;

Col. 15, line 36, delete the word "falter" and insert the word --filter --.

Signed and Sealed this

Fourth Day of February, 1997

Attest:

BRUCE LEHMAN

*Attesting Officer*   Commissioner of Patents and Trademarks